(12) United States Patent
Baranowski et al.

(10) Patent No.: US 11,998,440 B2
(45) Date of Patent: Jun. 4, 2024

(54) STENT-GRAFT PROSTHESIS WITH PRESSURE RELIEF PORTS

(71) Applicant: MEDTRONIC VASCULAR, INC., Santa Rosa, CA (US)

(72) Inventors: Ian Benjamin Baranowski, Santa Rosa, CA (US); Tessa Bronez, Santa Rosa, CA (US); Keith D. Perkins, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 17/184,329

(22) Filed: Feb. 24, 2021

(65) Prior Publication Data

US 2022/0265417 A1 Aug. 25, 2022

(51) Int. Cl.
*A61F 2/07* (2013.01)
*A61F 2/06* (2013.01)
*A61F 2/966* (2013.01)

(52) U.S. Cl.
CPC .............. *A61F 2/07* (2013.01); *A61F 2/9662* (2020.05); *A61F 2002/068* (2013.01); *A61F 2002/9665* (2013.01)

(58) Field of Classification Search
None
See application file for complete search history.

(56) References Cited

U.S. PATENT DOCUMENTS

| | | | |
|---|---|---|---|
| 6,398,803 B1 | 6/2002 | Layne et al. | |
| 7,955,373 B2 | 6/2011 | Sowinski et al. | |
| 8,852,267 B2 | 10/2014 | Cattaneo | |
| 8,882,828 B2 * | 11/2014 | Kinkade | A61F 2/95 623/2.11 |
| 8,992,593 B2 | 3/2015 | Chuter et al. | |
| 9,498,323 B2 * | 11/2016 | King | A61F 2/07 |
| 9,566,149 B2 | 2/2017 | Shaw | |
| 10,105,250 B2 | 10/2018 | Berra | |
| 10,159,558 B2 * | 12/2018 | Chuter | A61F 2/07 |

(Continued)

FOREIGN PATENT DOCUMENTS

| | | | | |
|---|---|---|---|---|
| EP | 2564811 A1 * | 3/2013 | | A61F 2/07 |
| EP | 2740439 A1 | 7/2014 | | |

(Continued)

OTHER PUBLICATIONS

EP Appln No. 19169027.0, Extend EP Search Report, dated Aug. 22, 2019, 8 pgs.

(Continued)

*Primary Examiner* — Ann Schillinger

(74) *Attorney, Agent, or Firm* — Medler Ferro Woodhouse & Mills PLLC

(57) ABSTRACT

A stent-graft prosthesis includes a graft material having a tubular construction, a frame coupled to the graft material, and a port or opening disposed between a proximal end and a distal end of the graft material. The port or opening is open during deployment of the stent-graft prosthesis to enable blood flow from a graft lumen within the graft material to exit the graft lumen, and the port or opening is blocked upon full deployment of the stent-graft prosthesis to prevent blood flow from within the graft lumen from exiting the graft lumen through the port or opening.

11 Claims, 32 Drawing Sheets

(56) References Cited

U.S. PATENT DOCUMENTS

| | | | |
|---|---|---|---|
| 11,284,989 B2 * | 3/2022 | Argentine | A61F 2/07 |
| 11,357,612 B2 * | 6/2022 | Shipley | A61F 2/07 |
| 2001/0032009 A1 | 10/2001 | Layne et al. | |
| 2006/0184089 A1 | 8/2006 | Makower et al. | |
| 2008/0109066 A1 * | 5/2008 | Quinn | A61F 2/07 623/1.13 |
| 2009/0276027 A1 | 11/2009 | Glynn | |
| 2010/0204784 A1 | 8/2010 | Molaei et al. | |
| 2011/0160833 A1 * | 6/2011 | Gonzalez | A61F 2/856 623/1.11 |
| 2011/0270378 A1 * | 11/2011 | Bruszewski | A61F 2/07 623/1.35 |
| 2012/0130478 A1 * | 5/2012 | Shaw | A61F 2/07 623/1.35 |
| 2012/0179235 A1 * | 7/2012 | Lazarus | A61F 2/07 623/1.13 |
| 2012/0221094 A1 * | 8/2012 | Cunningham | A61F 2/07 623/1.12 |
| 2012/0290069 A1 * | 11/2012 | Ivancev | A61F 2/07 623/1.13 |
| 2012/0296406 A1 | 11/2012 | Minion | |
| 2013/0172984 A1 | 7/2013 | Greenberg et al. | |
| 2014/0148888 A1 * | 5/2014 | Barrand | A61F 2/07 623/1.2 |
| 2015/0012080 A1 * | 1/2015 | Barrand | A61F 2/07 623/1.13 |
| 2015/0216684 A1 | 8/2015 | Enzmann et al. | |
| 2016/0324670 A1 * | 11/2016 | Yamaguchi | A61F 2/954 |
| 2017/0056215 A1 | 3/2017 | Nagesh et al. | |
| 2018/0303641 A1 * | 10/2018 | Roeder | A61F 2/07 |
| 2019/0321160 A1 | 10/2019 | Argentine et al. | |

FOREIGN PATENT DOCUMENTS

| | | | | |
|---|---|---|---|---|
| EP | 3053545 A1 * | 8/2016 | | A61F 2/07 |
| EP | 3342372 A1 * | 7/2018 | | A61F 2/06 |
| EP | 3560456 A1 * | 10/2019 | | A61F 2/07 |
| WO | 20110076408 A1 | 6/2011 | | |
| WO | 20170137868 A1 | 8/2017 | | |
| WO | WO-2017137868 A1 * | 8/2017 | | A61F 2/07 |

OTHER PUBLICATIONS

Extended European Search Report, EP Application No. 22156798.5, dated Jul. 27, 2022, 8 pages.

* cited by examiner

STENT-GRAFT PROSTHESIS WITH PRESSURE RELIEF PORTS

FIELD OF THE INVENTION

The present invention generally relates to stent-graft prostheses having pressure relief channels.

BACKGROUND OF THE INVENTION

Stent-graft prostheses are prostheses for percutaneous implantation in blood vessels or other similar body vessels or organs of the living body. These stent-graft prostheses typically include one or more radially compressible stents that can be expanded to a diameter slightly larger than a target body vessel, and a graft material interior or exterior of the stent. When the stent-graft prosthesis is radially expanded in situ, the one or more stents anchor the tubular graft material to the wall of the body vessel. Thus, stent-graft prostheses are typically held in place by mechanical engagement and friction due to the opposition forces provided by the radially expanded stents against the vessel wall. When the one or more stents are expanded, the graft material is anchored on the interior wall of the body vessel. Thus, the graft material is held in place by the friction between the one or more stents and the body vessel.

Stent-graft prostheses are often utilized for treating aneurysms, dissections and transections. In an example, an aneurysm may result from weak, thinned blood vessel walls that "balloon" or expand due to aging, disease and/or blood pressure in the vessel. These aneurysmal blood vessels have a potential to rupture, causing internal bleeding and potentially life threatening conditions. When the stent-graft prosthesis is implanted within an aneurysmal blood vessel, with the stent-graft prosthesis extending proximal and distal of the aneurysm, the stent-graft prosthesis acts as a bypass lumen that permits blood to flow through the graft material instead of the expanded section of the aneurysm. Stent-graft prostheses, therefore, isolate aneurysms or other blood vessel abnormalities from normal blood pressure, reducing pressure on the weakened vessel wall and reducing the chance of vessel rupture.

Stent-graft prostheses may have an open-web configuration or a closed-web configuration. In an open-web configuration, the end of the frame (stent(s)) of the stent-graft prosthesis extends beyond a corresponding end of the graft material, and thus has a portion that is not covered by the graft material. The uncovered portion generally permits blood flow into the stent-graft prosthesis during implantation. The uncovered portion of the open-web configuration further provides a convenient location for coupling to a tip-capture mechanism of a delivery catheter. In the closed-web configuration, the end of the frame (stent(s)) of the stent-graft prosthesis is covered or lined by the graft material. Thus, the closed-web configuration has no exposed stents and is intended to reduce potential trauma between the stent-graft prosthesis and the vessel. For example, stent-graft prostheses having a closed-web configuration may be selected to treat aneurysms, dissections or vessel transections due to the delicate condition of the vessel tissue. A closed-web configuration stent-graft prosthesis thus is less traumatic to sensitive tissues and disease states. A closed-web configuration stent-graft prosthesis offers convenience by preserving the structural integrity of fragile blood vessel tissues.

For implantation within a blood vessel, the stent-graft prosthesis is deployed through a minimally invasive intraluminal delivery procedure. More particularly, a body lumen or vasculature is accessed percutaneously at a convenient entry point, such as a femoral artery, and the stent-graft prosthesis is routed through the vasculature to the desired treatment location. For example, a self-expanding stent-graft prosthesis may be compressed and disposed within a distal end of an outer shaft or sheath component of a delivery catheter as part of a delivery system. A proximal or upstream end of the stent-graft prosthesis may be removably coupled to a tip capture mechanism of an inner shaft or member. The delivery system is then maneuvered, typically tracked through a body lumen until a distal end of the delivery system and the stent-graft prosthesis are positioned at the intended treatment site. The outer sheath of the delivery system is withdrawn. The tip capture mechanism prevents the stent-graft prosthesis from being withdrawn with the outer sheath, and further prevents the proximal or upstream end of the stent-graft prosthesis from fully expanding. In a situation where a tip capture mechanism is not used, or the upstream end of the stent-graft prosthesis is released from the tip capture mechanism prior to the downstream end of the stent-graft prosthesis being fully deployed, or blood may enter the lumen of the stent-graft prosthesis when attached to the tip capture mechanism, blood flow may enter the stent-graft prosthesis from the upstream end and not have a way to escape the stent-graft prosthesis. This pressure from the blood flow may lead to "windsocking" or a "windsock" effect. This is windsock effect is due to high pressures and flow rates in the aorta entering the stent-graft prosthesis, thereby forcing it downstream that may lead to inaccurate deployment/stent-graft migration. This windsock effect may also take place in situations where a tip capture mechanism is used. The windsock effect may be reduced by cardiac pacing and/or medication that induces hypotension. However, these solutions risk other complications in patients that have advanced diseases and/or co-morbidities.

Accordingly, there is a need for stent-graft prostheses minimizing the windsock effect while effectively isolating the diseased portion of the vessel when fully deployed.

BRIEF SUMMARY OF THE INVENTION

Embodiments hereof relate to a stent-graft prostheses including a graft material having a tubular construction, a frame coupled to the graft material, and a port or opening disposed between a proximal end and a distal end of the graft material. The port or opening is open during deployment of the stent-graft prosthesis to enable blood flow from a graft lumen within the graft material to exit the graft lumen, and the port or opening is blocked upon full deployment of the stent-graft prosthesis to prevent blood flow from within the graft lumen from exiting the graft lumen through the port or opening In first aspect hereof, a stent-graft prosthesis includes: a graft material having a tubular construction, the graft material including a proximal end, a distal end, and a graft lumen extending between the proximal end and the distal end; a frame coupled to the graft material; and a port disposed between the proximal end and the distal end of the graft material, wherein the port enables blood flow from the within the graft lumen to exit the graft lumen, wherein the graft material includes an unsupported graft portion between adjacent frame members of the frame, and wherein the stent-graft prosthesis is configured to be folded in situ in the unsupported graft portion into a folded configuration such that the port is blocked to prevent blood flow from within the graft lumen from exiting the graft lumen through the port.

In a second aspect hereof, the stent-graft prosthesis according to the first aspect hereof includes the unsupported graft portion in the range of 4 mm to about 40 mm, or about 10 mm to about 30 mm, or about 15 mm to about 25 mm in length.

In a third aspect hereon, the stent-graft prosthesis according to the first or second aspects hereof includes a plurality of ports disposed around a circumference of the graft material.

In a fourth aspect hereof, the stent-graft prosthesis according to any of the first to third aspects, in the folded configuration, includes the unsupported portion folded such that at least a portion of the unsupported portion is disposed within the graft lumen of the graft material proximal of the unsupported portion.

In a fifth aspect hereof, the stent-graft prosthesis according to the fourth aspect hereof, in the folded configuration, includes a first frame member that is distal of the unsupported portion when not in the folded configuration disposed within a second frame member that is proximal of the unsupported portion when not in the folded configuration.

In a sixth aspect hereof, a stent-graft prosthesis includes: a graft material having a tubular construction, the graft material including a proximal end, a distal end, and a graft lumen extending between the proximal end and the distal end; a frame coupled to the graft material; a port disposed between the proximal end and the distal end of the graft material, wherein the port enables blood flow from within the graft lumen to exit the graft lumen; and a port closing stent disposed within the graft lumen, wherein the port closing stent includes a first end attached to an inner surface of the graft material and a second end not attached to the graft material, wherein the port closing stent includes a first configuration wherein the port closing stent is spaced from the port so as to permit blood flow from the graft lumen through the port and a second configuration wherein the port closing stent blocks flow from the graft lumen through the port.

In a seventh aspect hereof, in the stent-graft prosthesis according to the sixth aspect hereof, the port closing stent includes port closing graft material attached thereto such that in the second configuration the port closing graft material blocks the port.

In an eighth aspect hereof, in the stent-graft prosthesis according to the sixth or seventh aspect hereof, in the first configuration, the second end of the port closing stent is in a radially compressed configuration, and in the second configuration, the second end of the port closing stent is in a radially expanded configuration.

In a ninth aspect hereof, in the stent-graft prosthesis according to any of the sixth to eighth aspects hereof, the second end of the port closing stent is configured to be maintained in a radially compressed configuration by a sheath of a delivery system such that retraction of the sheath causes the second end of the port closing stent to radially expand to a radially expanded configuration.

In a tenth aspect hereof, in the stent-graft prosthesis according to any of the sixth to eighth aspects hereof, the second end of the port closing stent is maintained in a radially compressed configuration by a circumferentially restraining suture and a trigger wire such that moving the trigger wire causes the second end of the port closing stent to radially expand to a radially expanded configuration.

In an eleventh aspect hereof, in the stent-graft prosthesis according to any of the sixth to tenth aspects hereof, the first end of the port closing stent is a proximal end of the port closing stent and the second end of the port closing stent is a distal end of the port closing stent.

In a twelfth aspect hereof, in the stent-graft prosthesis according to any of the sixth to tenth aspects hereof, the first end of the port closing stent is a distal end of the port closing stent and the second end of the port closing stent is a proximal end of the port closing stent.

In a thirteenth aspect hereof, in the stent-graft prosthesis according to any of the sixth to twelfth aspects hereof, the stent-graft prosthesis further includes a skirt coupled to an outer surface of the graft material, wherein the skirt covers the port.

In a fourteenth aspect hereof, in the stent-graft prosthesis according to the thirteenth aspect hereof, the skirt circumscribes a circumference of the graft material, where the skirt includes a first end attached to the graft material and a second end that is not attached to the graft material.

In a fifteenth aspect hereof, in the stent-graft prosthesis according to the thirteenth or fourteenth aspect hereof, the skirt further includes a stent attached thereto.

In a sixteenth aspect hereof, a stent-graft prosthesis includes: an outer stent-graft including an outer graft material having a tubular construction, the outer graft material comprising a proximal end, a distal end, and a graft lumen extending between the proximal end and the distal end, an outer frame coupled to the outer graft material, and a port disposed between the proximal end and the distal end of the outer graft material, wherein the port enables blood flow from within the graft lumen to exit the outer graft lumen; and an inner stent-graft disposed within the graft lumen of the outer stent-graft, wherein the inner stent-graft includes an inner graft material and an inner frame coupled to the inner graft material, wherein the inner stent-graft includes a radially compressed configuration wherein the inner stent-graft is spaced from the port so as to permit blood flow from the graft lumen through the port and a radially expanded configuration wherein the inner stent-graft blocks flow from the graft lumen through the port.

In a seventeenth aspect of the invention, in the stent-graft prosthesis according to the sixteenth aspect hereof, the port comprises a mesh portion of the outer graft material that extends around the circumference of the outer graft material.

In an eighteenth aspect of the invention, in the stent-graft prosthesis according to the sixteenth aspect hereof, the port comprises a plurality of ports.

In a nineteenth aspect of the invention, in the stent-graft prosthesis according to any of the sixteenth to eighteenth aspects hereof, the inner stent-graft is configured to be maintained in the radially compressed configuration by a sheath of a delivery system such that retraction of the sheath causes the inner stent-graft to radially expand to the radially expanded configuration.

In a twentieth aspect of the invention, in the stent-graft prosthesis according to any of the sixteenth to eighteenth aspects hereof, the inner stent-graft is maintained in the radially compressed configuration by circumferentially restraining sutures and a trigger wire such that moving the trigger wire causes the inner stent-graft to radially expand to the radially expanded configuration.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Figure 1:
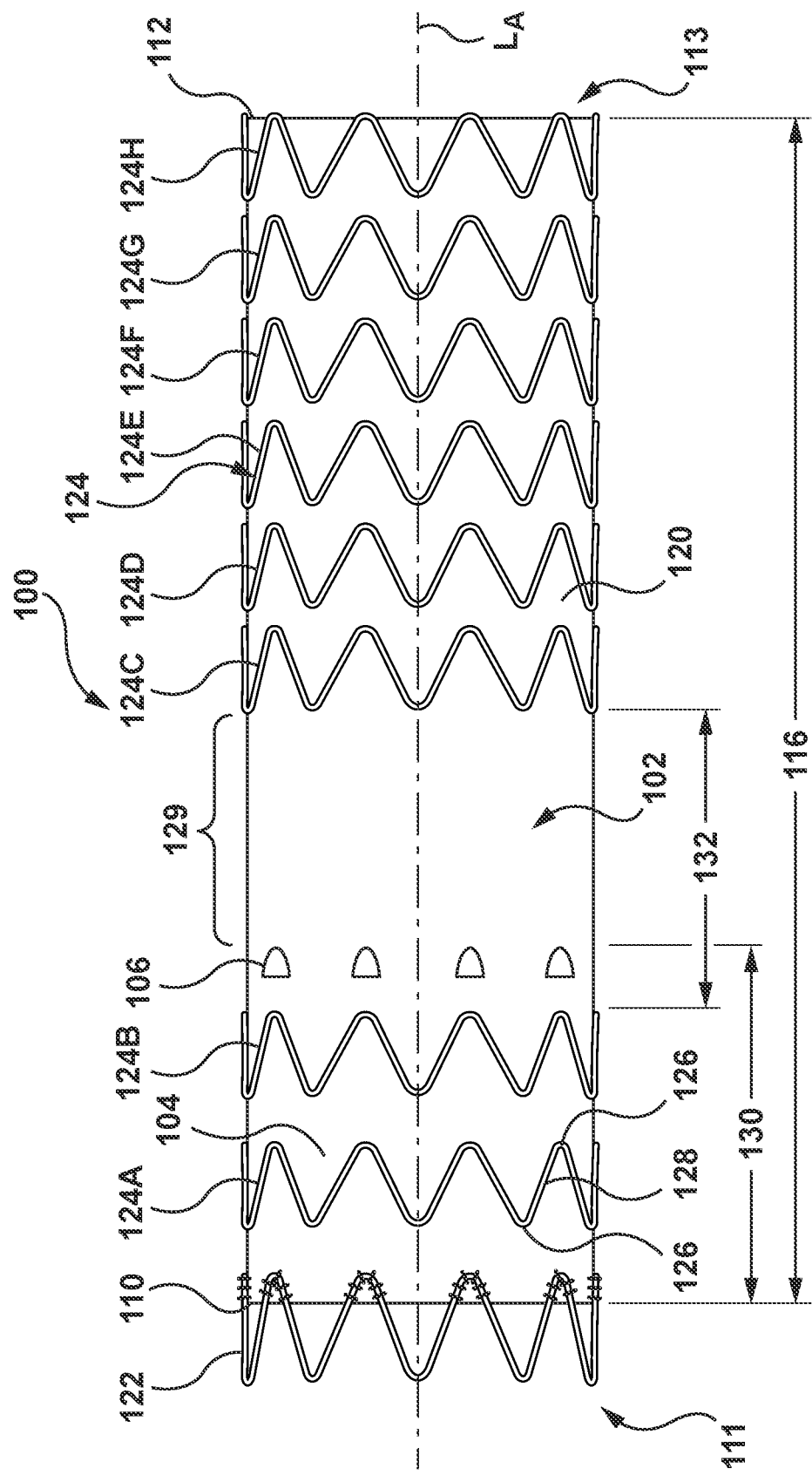
FIG. 1 depicts a schematic side view illustration of a stent-graft prosthesis in a radially expanded configuration according to an embodiment hereof.

Specific embodiments of the present invention are now described with reference to the figures, wherein like reference numbers indicate identical or functionally similar elements. The terms "distal" and "proximal", when used in the following description to refer to a catheter and/or other system components hereof are with respect to a position or direction relative to the treating clinician. Thus, "distal" and "distally" refer to positions distant from or in a direction away from the treating clinician, and the terms "proximal" and "proximally" refer to positions near or in a direction toward the treating clinician. The terms "distal" and "proximal", when used in the following description to refer to a native vessel or a device to be implanted into a native vessel, such as a stent-graft prosthesis, are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

In addition, the term "self-expanding" is used in the following description with reference to one or more stent structures of the stent-graft prosthesis, and is intended to convey that the structures are shaped or formed from a material that can be provided with a mechanical memory to return the structure from a radially compressed or collapsed configuration to a radially expanded configuration. Non-exhaustive exemplary self-expanding materials include stainless steel, a pseudo-elastic metal such as a nickel titanium alloy (e.g. NITINOL), various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy (e.g. NITINOL).

The following detailed description is not intended to limit the invention or the application and uses of the invention. Although the description of the invention is in the context of the treatment of blood vessels such as the aorta, the invention may also be used in any other body passageways where it is deemed useful, non-limiting examples of which include coronary arteries, carotid arteries, and renal arteries. Therefore, the term body vessel, or vessel, is used to apply to the body passageways as a whole. Furthermore, there is no intention to be bound by any expressed or implied theory presented in the preceding technical field, background, brief summary or the following detailed description.

A stent-graft prosthesis in accordance with embodiments hereof includes at least one port configured to permit blood flow from within a central channel or lumen of the stent-graft prosthesis to exit the central channel of the stent-graft prosthesis as the stent-graft prosthesis is transitioning from a radially compressed configuration for delivery to a radially expanded configuration when deployed. The stent-graft prosthesis also includes a means to close the ports when the stent-graft prosthesis in the fully radially expanded configuration such that blood can only exit the stent-prosthesis through the downstream end of the stent-graft prosthesis after the stent-graft prosthesis is fully deployed.

FIGS. 1-9 illustrate a stent-graft prosthesis 100 according to embodiments hereof. As shown in FIG. 1, the stent-graft prosthesis 100 includes a graft material 102, a frame 104, and openings or ports 106 extending from an inner surface 118 to an outer surface 120 of the graft material 102. The stent-graft prosthesis 100 has a radially compressed configuration for delivery, a radially expanded configuration when deployed, and a partially expanded configuration when transitioning between the radially compressed and the radially expanded configurations. When the stent-graft prosthesis 100 is in the radially expanded configuration at a desired treatment location, the stent-graft prosthesis 100 is configured to bypass a vessel abnormality such as an aneurysm within a body vessel. While described herein as configured to bypass an aneurysm, such as an abdominal aortic aneurysm, this is by way of example and not limitation, and the stent-graft prosthesis 100 may be configured to support/bypass other vessel abnormalities such as, but not limited to dissections and transections.

The graft material 102 is of a generally tubular shape having a central longitudinal axis $L_A$, a first end or edge 110, a second end or edge 112, and a graft lumen or central passage 114 extending from the first end 110 to the second end 112. The graft material 102 has a longitudinal length 116, which may vary based upon the application. The first end 110 of the graft material 102 may be referred to as a proximal or an upstream end or edge of the graft material 102. In the embodiment shown, the first, proximal or upstream end or edge 111 of the stent-graft prosthesis 100 does not coincide with the first end 110 of the graft material 102 because a portion of the frame 104 extends past the first end 110 of the graft material 102. The second end 112 of the graft material 102 may be referred to as a distal or a downstream end or edge of the graft material 102. In the embodiment shown, the second end 112 of the graft material 102 is also a second, distal, or downstream end or edge 113 of the stent-graft prosthesis 100. For a stent-graft prosthesis for an abdominal aortic aneurysm delivered from the femoral artery, the proximal or upstream end 111 of the stent-graft prosthesis 100 is the end that may be coupled to a tip capture or retainer mechanism of a delivery system. The distal or downstream end 113 may also be coupled to a retainer or similar mechanism of the delivery system. The graft material 102 may be formed from any suitable graft material, for example and not way of limitation, the graft material 102 may be formed from a low-porosity woven or knit polyester, DACRON material, expanded polytetrafluoroethylene, polyurethane, silicone, or other suitable materials. In another embodiment, the graft material could also be a natural material such as pericardium or another membranous tissue such as intestinal submucosa.

In the embodiment of FIGS. 1-9, the frame 104 of the stent-graft prosthesis 100 includes a sealing or seal stent 122 and a plurality of body stents 124. The frame 104 is configured to support the graft material 102. The seal stent 122 and the body stents 124 may also be referred to as frame members. The seal stent 122 and each of the body stents 124 of the frame 104 are coupled to the graft material 102. In the embodiment illustrated in FIG. 1, the stent-graft prosthesis 100 is shown in the radially expanded configuration and includes one (1) seal stent 122 adjacent to the first end 110, and eight (8) body stents 124A-124F axially or longitudinally spaced between the first end 110 and the second end 112 of the graft material 102. Although shown with eight (8) body stents 124, it will be understood that the stent-graft prosthesis 100 may include more or fewer body stents 124 depending upon the desired length 116 of the stent-graft prosthesis 100 and/or the intended application. Further, instead of a plurality of stents, the frame 104 may be a helically wound stent, as known to those skilled in the art, or a combination of helically wound stent(s) and cylindrical stents. The seal stent 122 and each of the body stents 124 are self-expanding and each includes a radially compressed state, a partially expanded state, and a radially expanded state. Accordingly, the seal stent 122 and each of the body stents 124 are constructed from self-expanding materials as described previously. The seal stent 122 and each of the body stents 124 may be sinusoidal patterned rings including a plurality of crowns or bends 126 and a plurality of struts or straight segments 128 with each crown 126 being formed between a pair of adjacent struts 128. While the seal stent 122 and the body stents 124 are shown in FIG. 1 as having a similar sinusoidal pattern, it will be understood that the seal stent 122 and the body stents 124 may have different patterns or configurations. The seal stent 122 and the body stents 124 are coupled to the graft material 102 by stitches, sutures, or other suitable methods. In the embodiment of FIG. 1, the seal stent 122 and the body stents 124 are coupled to the outer surface 120 of the graft material 102. However, the seal stent 122 and the body stents 124 alternatively may be coupled to the inner surface 118 of the graft material 102. When the stent-graft prosthesis 100 is used for treating an aneurysm, the seal stent 122 is configured with sufficient radial spring force and flexibility to conformingly engage the stent-graft prosthesis 100 with the body lumen inner wall, to avoid excessive leakage, and to prevent pressurization of the aneurysm, i.e., to provide a leak-resistant seal.

Figure 2:
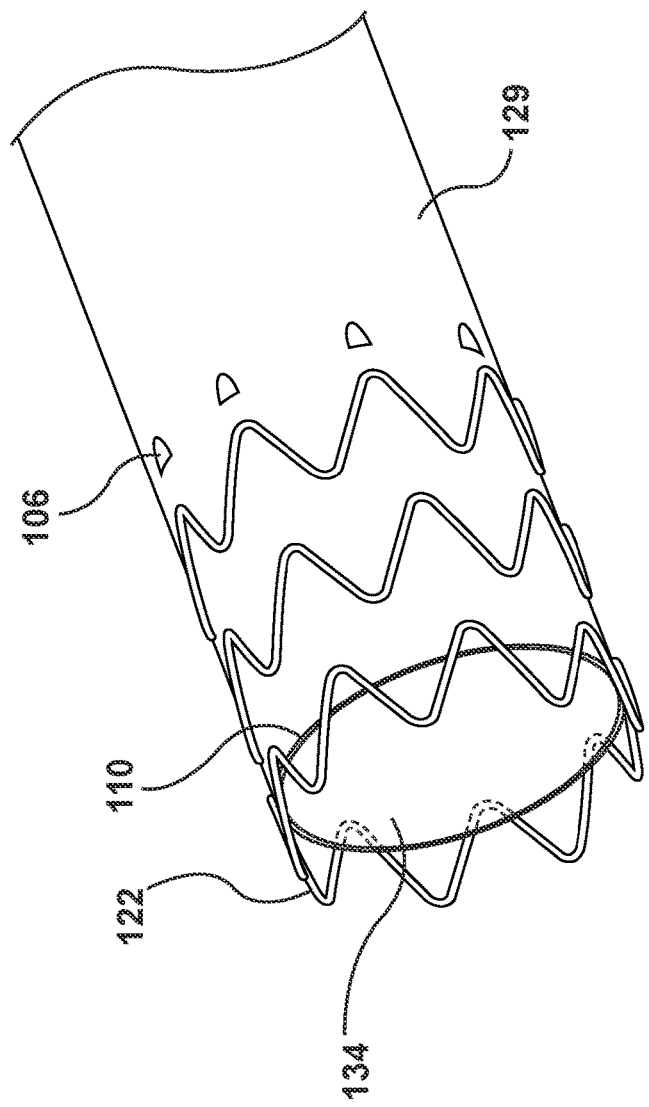
FIG. 2 depicts a schematic perspective of a first end of the stent-graft prosthesis of FIG. 1 in the radially expanded configuration.

As briefly explained above, in the embodiment of FIG. 1, the proximal end 111 of the stent-graft prosthesis 100 has an open-web configuration in which the endmost crowns 126 of the seal stent 122 extend proximal of the first end 110 of the graft material 102, as shown in FIGS. 1 and 2. As utilized herein, "endmost" crowns are the crowns, peaks, or apexes of a stent that are most proximate the end or edge of the stent-graft prosthesis 100 in the direction of the end or edge, such as the first end 111. As viewed in FIG. 1, the stent-graft prosthesis 100 includes a closed-web configuration at the distal end 113, with the endmost crowns 126 of the distal-most body stent 124H covered or lined by the material graft 102, i.e., they do not extend outside of or beyond the second end 112 of the graft material 102. In other embodiments hereof (not shown), the first end 111 and second end 113 of the stent-graft prosthesis 100 may both be an open-web configuration, may both be a closed-web configuration, or the first end 111 may be a closed-web configuration and the second end 113 may be an open-web configuration.

Figure 2B:
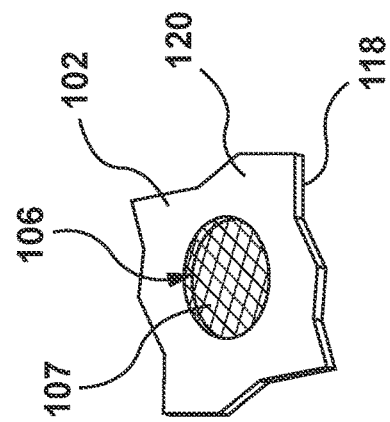
FIGS. 2A and 2B depict illustrations of embodiments of ports of the stent-graft prosthesis of FIG. 1.
Figure 2A:
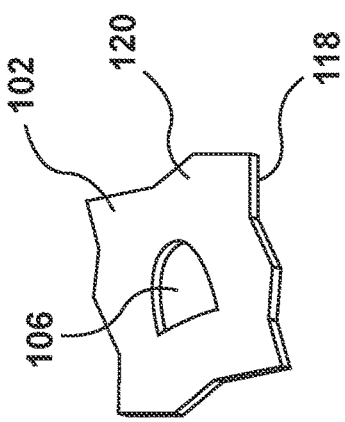

The plurality of ports 106 are configured to permit blood flow to escape the central passage 114 of the graft material 102 when the stent-graft prosthesis 100 is in the partially expanded configuration, as explained in more detail below. Accordingly, when the stent-graft prosthesis 100 is in the partially expanded configuration, the ports 106 are configured to relieve pressure associated with pulsatile blood flow on the stent-graft prosthesis 100 during implantation within a body vessel. The partially expanded configuration, as used herein, means that a portion or portions of the stent-graft prosthesis 100 are in a radially compressed state, portions of the stent-graft prosthesis 100 are in a partially expanded state, and portions of the stent-graft prosthesis 100 may be in a radially expanded state, as will be described below. As shown in FIGS. 1 and 2, the ports 106 are located at the distal crowns 126 of the body stent 124B. However, this is not meant to be limiting, and the ports 106 can be located elsewhere. Further, the number and size of the ports 106 can be selected to provide the proper amount of blood flow out of the graft lumen 114 during deployment of the stent-graft prosthesis 100. In embodiments, the ports 106 may be shorter in longitudinal length if made larger in the circumferential direction. In some embodiments, the ports 106 may a thin (longitudinally) band of small laser cut holes. I some embodiments, rather than holes in the graft material, a section of permeable material may replace the graft material in the portion where the pressure relied is desired, i.e. where the ports would be located. In embodiments, the ports 106 are evenly distributed around the circumference of the stent-graft prosthesis 100. In the embodiment shown, the ports 106 are disposed at the same the longitudinal location along the graft material 102. In other words, each of the ports 106 is located a distance 130 from the first end 110 of the graft material 102. However, this is not meant to be limiting, and the ports 106 may be located at different longitudinal locations. Further, the ports 106 in the embodiment shown may be described as a single row of ports 106. However, this is also not meant to be limiting, and multiple rows of ports 106 are contemplated. Further, the ports 106 need not be located after the second body sent 124B. Instead, the ports 106 may be located longitudinally to enable blood flow therethrough until the stent-graft prosthesis 100 is sufficiently deployed such that the stent-graft prosthesis 100 will hold its position in the vessel. The ports 106 may be openings through the graft material 102, as shown in FIG. 2A. In other embodiments, such as shown in FIG. 2B, the ports 106 may include a mesh covering 107 covering the port 106. The mesh covering 107 includes openings of sufficient size to permit blood flow therethrough. The mesh covering 107 may cover an outer surface of the graft material 102, an inner surface of the graft material 102, or both inner and outer surfaces of the graft material 102.

In the embodiment shown, there is an unsupported graft portion 129 disposed between the ports 106 and the body stents 124 distal of the ports 106. By "unsupported graft portion", it is meant that no stents are attached to the graft material in this region. The unsupported graft portion 129 extends a longitudinal length of the graft material 102 without any stents at any portion of the circumference of the graft material 102. As described in more detail below, the unsupported graft portion 129 is of sufficient length to enable the graft material 102 to be folded under the ports 104 during deployment of the stent-graft prosthesis 100 prior to full deployment of the stent-graft prosthesis 100 to block the ports 106 such that blood flow out from the graft lumen 114 through the ports 106 is prevented after full deployment of the stent-graft prosthesis 100. In embodiments, the length 132 of the unsupported graft portion 129 between the distal-most body stent 124 proximal of the unsupported graft portion 129 and the proximal-most body stent 124 distal of the unsupported graft portion 129 (e.g., in the embodiment shown the distance between the body stent 124B and the body stent 124C) may be in the range of about 4 mm to about 40 mm, or about 10 mm to about 30 mm, or about 15 mm to about 25 mm. In some embodiments, the length 132 of the unsupported portion may be in a range of about two times to 10 times a longitudinal length of the ports 106, or in a range of about two times to about five times a longitudinal length of the ports 106, or in a range of about four times to about eight times a longitudinal length of the ports 106, or in a range of about five times to about six times a longitudinal length of the ports 106. In some embodiments, the length 132 is two times to six times, or two times to five times, or three times to four times, a longitudinal length between the distal crowns and the proximal crowns of the next adjacent body stents to the body stents defining the unsupported portion 129. In other words, in the present embodiment, the "next adjacent body stents" are the body stent 124D, 124E. In some embodiments, the length 132 is sufficient such that when folded such that the next adjacent distal body stent (body stent 124C in this embodiment) is disposed within the proximal adjacent body stent (body stent 124B in this embodiment), a longitudinal length between the distal crowns of the body stents 124B/C to the proximal crowns of the body stent 124D is consistent with a longitudinal length between the distal and proximal crowns of other body adjacent body stents, such as a longitudinal length between the distal crown of the body stent 124D and the proximal crown of the body stent 124E. The term "consistent" as used in this context means that the lengths are within 10% of each other.

The operation of the stent-graft prosthesis 100 will now be explained with reference to FIGS. 3-9, which are sectional cutaway views of a vessel illustrating the delivery, positioning and deployment of the stent-graft prosthesis 100 at the site of a vessel abnormality, which in FIGS. 3-9 is an aneurysm. However, this is by way of example and not limitation and embodiments of the stent-graft prosthesis 100 may be utilized with other vessel abnormalities including, but not limited to dissections and transections.

Figure 3:
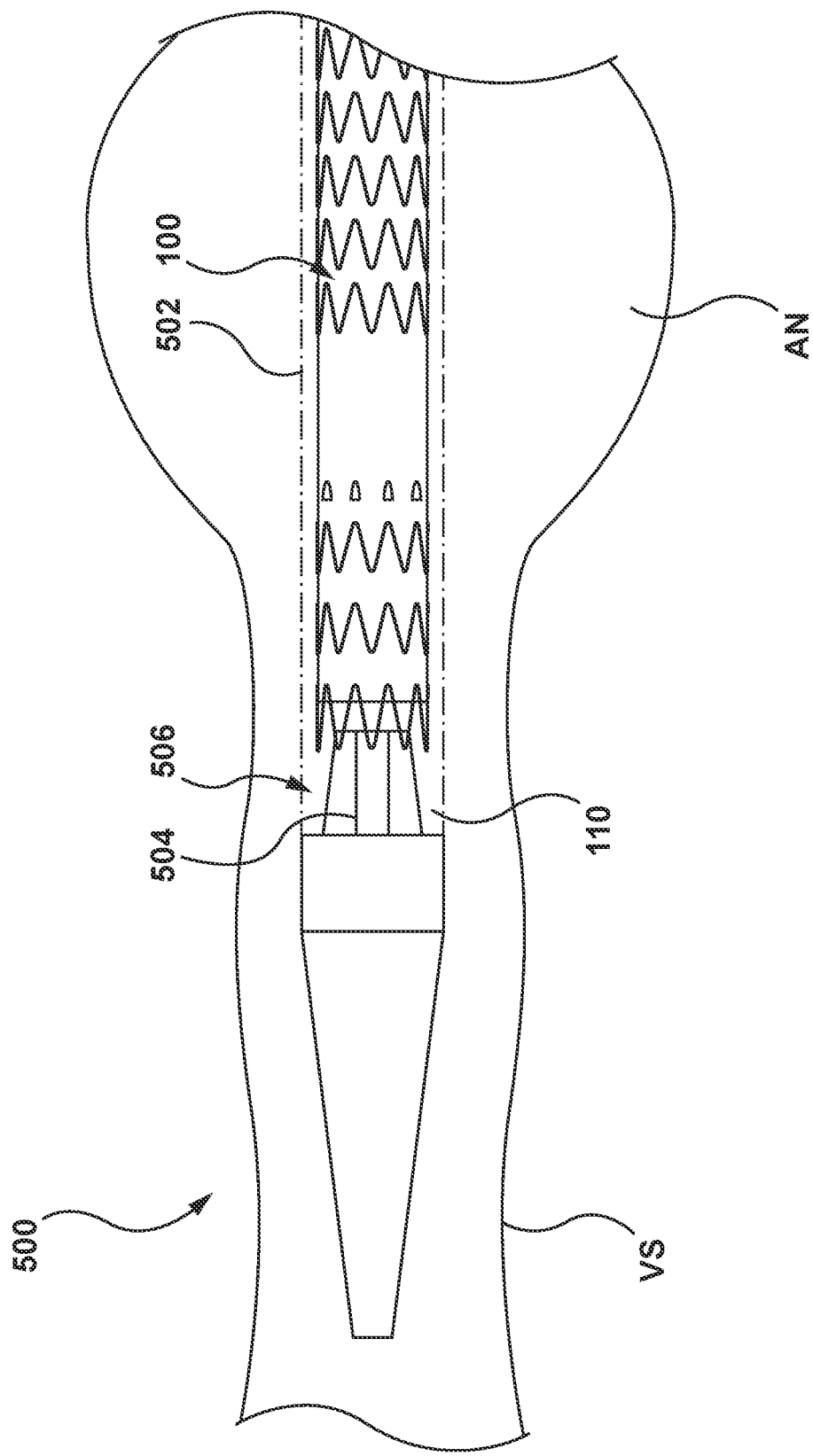
FIG. 3 depicts an illustration of a side view of the stent-graft prosthesis of FIG. 1 in situ, wherein the stent-graft prosthesis is disposed on a distal portion of a delivery system in a radially compressed configuration.

Referring now to FIG. 3, the stent-graft prosthesis 100 is disposed on a distal portion of a delivery system 500 in the radially compressed configuration. The delivery system 500 includes at least an outer sheath 502 and an inner shaft 504 that may have a tip capture mechanism 506 mounted thereon. In some embodiments, the proximal end 111 of the stent-graft prosthesis 100 is releasably coupled to the tip capture mechanism 506. The stent-graft prosthesis 100 is mounted on the inner shaft 504 and the outer sheath 502 encapsulates, covers, or restrains the stent-graft prosthesis 100 in the radially compressed configuration for delivery thereof. The delivery system 500 is advanced to a desired treatment location of an aneurysm AN in a vessel VS. In embodiments hereof, the delivery system 500 may be similar to the Captiva Delivery System, manufactured by Medtronic Vascular, Inc. of Santa Rosa, California, or a delivery system as described in U.S. Patent Application Publication No. 2009/0276027 to Glynn, or U.S. Pat. No. 8,882,828 to Kinkade et al., each of which is incorporated by reference herein in its entirety.

Figure 4:
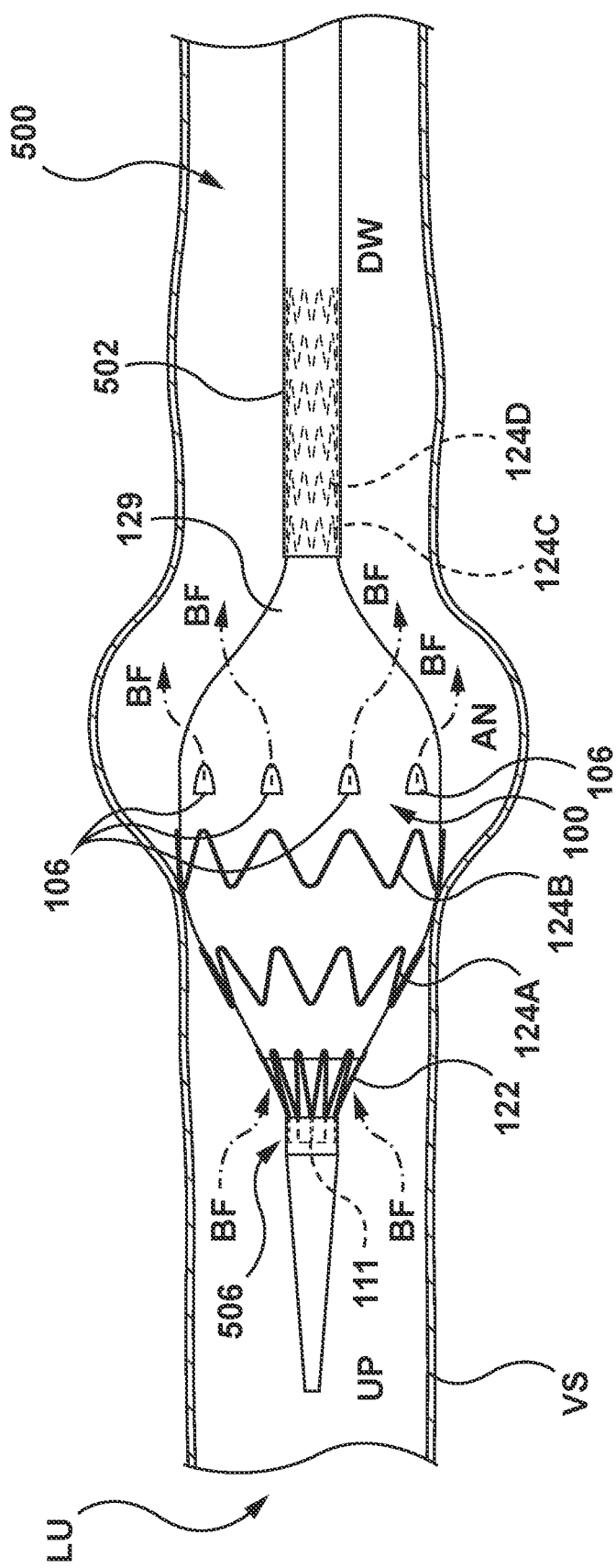
FIG. 4 depicts an illustration of a side view of the stent-graft prosthesis of FIG. 1 in situ, in a partially expanded configuration.

Once the stent-graft prosthesis 100 is at the desired treatment location within the vessel VS, the stent-graft prosthesis 100 may be deployed from the delivery system 500. The outer sheath 502 of the delivery system 500 is retracted to release a portion the stent-graft prosthesis 100. The released portion of the stent-graft prosthesis 100 radially expands within the vessel VS and the stent-graft prosthesis 100 transitions to a partially expanded configuration, as shown in FIG. 4. When in the partially expanded configuration shown in FIG. 4, the first end 111 of the stent-graft prosthesis is restrained in the radially compressed state by the tip capture mechanism 506. At least the distal end 113 of the stent graft prosthesis is restrained in the radially compressed state by the outer sheath 502. At the deployment moment shown in FIG. 4, the portion of the stent-graft prosthesis 100 restrained by the outer sheath 502 includes the body stents 124C-124H. As can be seen in FIG. 4, a portion of the stent-graft prosthesis 100, extending from the tip capture mechanism 506 of the delivery system 500 to a location between the body stent 124A and the body stent 124B, expands outwardly. Another portion of the stent-graft prosthesis 100, in FIG. 4 including the body stent 124B and the ports 106, is in the radially expanded configuration. Between the radially expanded portion and the portion restrained within the outer sheath 502 is a tapered portion tapering from the radially expanded configuration to the radially compressed configuration restrained within the outer sheath 502.

When in the partially expanded configuration of FIG. 4, the stent-graft prosthesis 100 generally occludes the lumen LU of the vessel VS. Thus, blood flow does not pass within the lumen LU of the vessel VS around the outside of the stent-graft prosthesis 100. Further, in other embodiments without a tip capture mechanism or with longer threads coupling the upstream portion of the stent-graft prosthesis to the tip capture mechanism, the portion of the stent-graft prosthesis 100 upstream of the ports 106 would also occlude the lumen LU of the vessel. In either situation, blood may enter within the graft lumen 114 of the graft material 102 via an opening 134 at the first end 110 of the graft material 102. However, as explained above, blood entering the graft lumen 114 of the graft material 102 may lead to "windsocking" or a "windsock" effect. However, with the stent-graft prosthesis 100, blood that enters the graft lumen 114 of the graft material 102 can exit through the ports 106, as shown in FIG. 4. Thus, blood from an upstream side UP of the stent-graft prosthesis 100 is permitted to travel into the stent-graft prosthesis 100, out of the stent-graft prosthesis 100 through the ports 106 to the downstream side DW of the stent-graft prosthesis 100. More precisely, blood on the upstream side UP of the stent-graft prosthesis 100 enters the graft lumen 114 of the stent-graft prosthesis 100 through the opening 134 the first end 110 of the graft material 102, travels through the graft lumen 114 of the stent-graft prosthesis 100, and exits to the downstream side DW of the stent-graft prosthesis 100 through the ports 106. The exit of the blood flow through the ports 106 relieves pressure build-up within the stent-graft prosthesis 100. Further, the flow of blood through the ports 106 from the upstream side UP to the downstream side DW of the stent-graft prosthesis 100 provides blood supply to vessels downstream of the stent-graft prosthesis 100. When the pressure associated with the pulsatile blood flow is relieved by the ports 106 during deployment of the stent-graft prosthesis 100, the stent-graft prosthesis 100 can be more precisely positioned. In addition, the position of the stent-graft prosthesis 100 can be more easily maintained during deployment of the stent-graft prosthesis 100.

Figure 5:
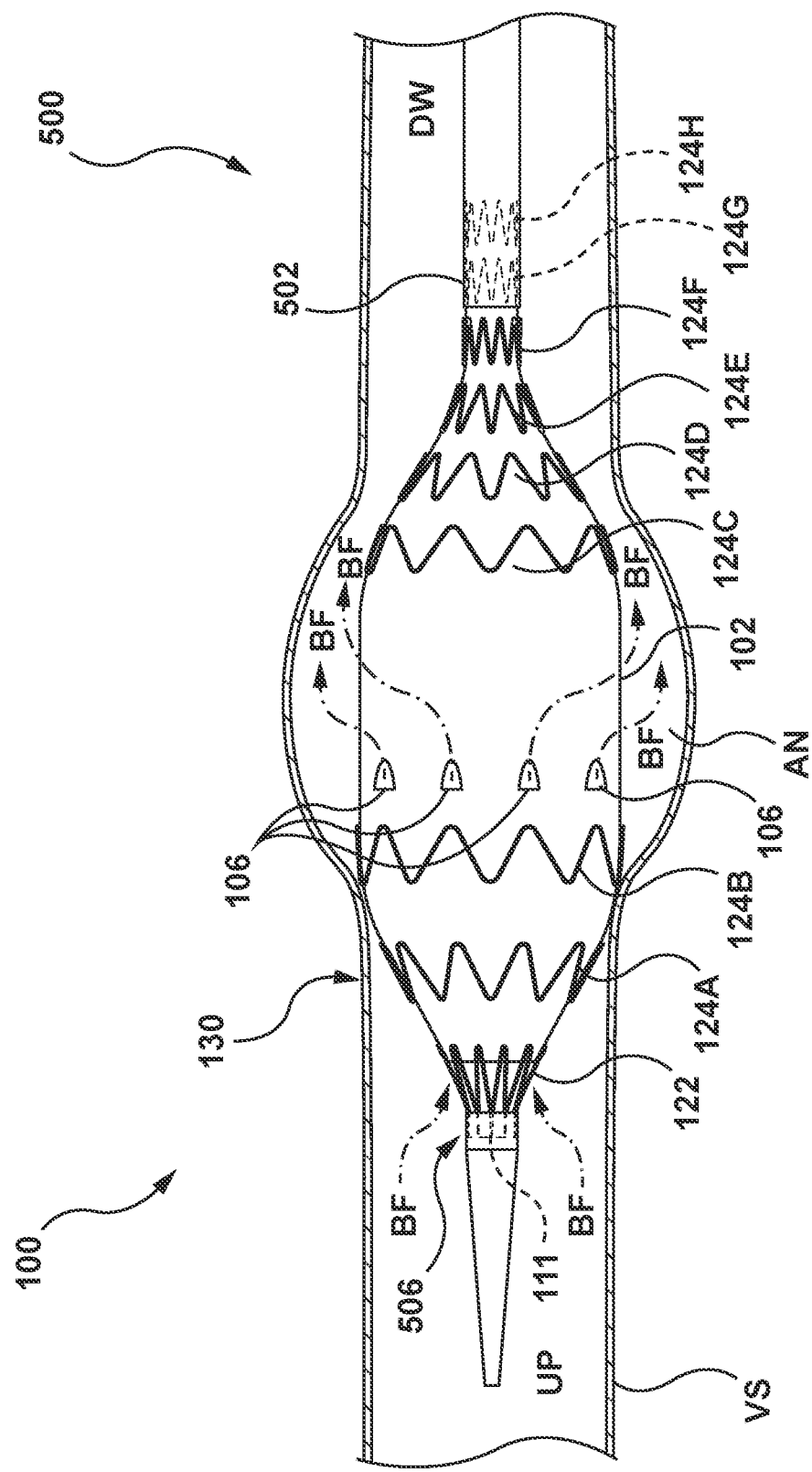
FIG. 5 depicts an illustration of a side view of the stent-graft prosthesis of FIG. 1 in situ, in a partially expanded configuration.
Figure 6:
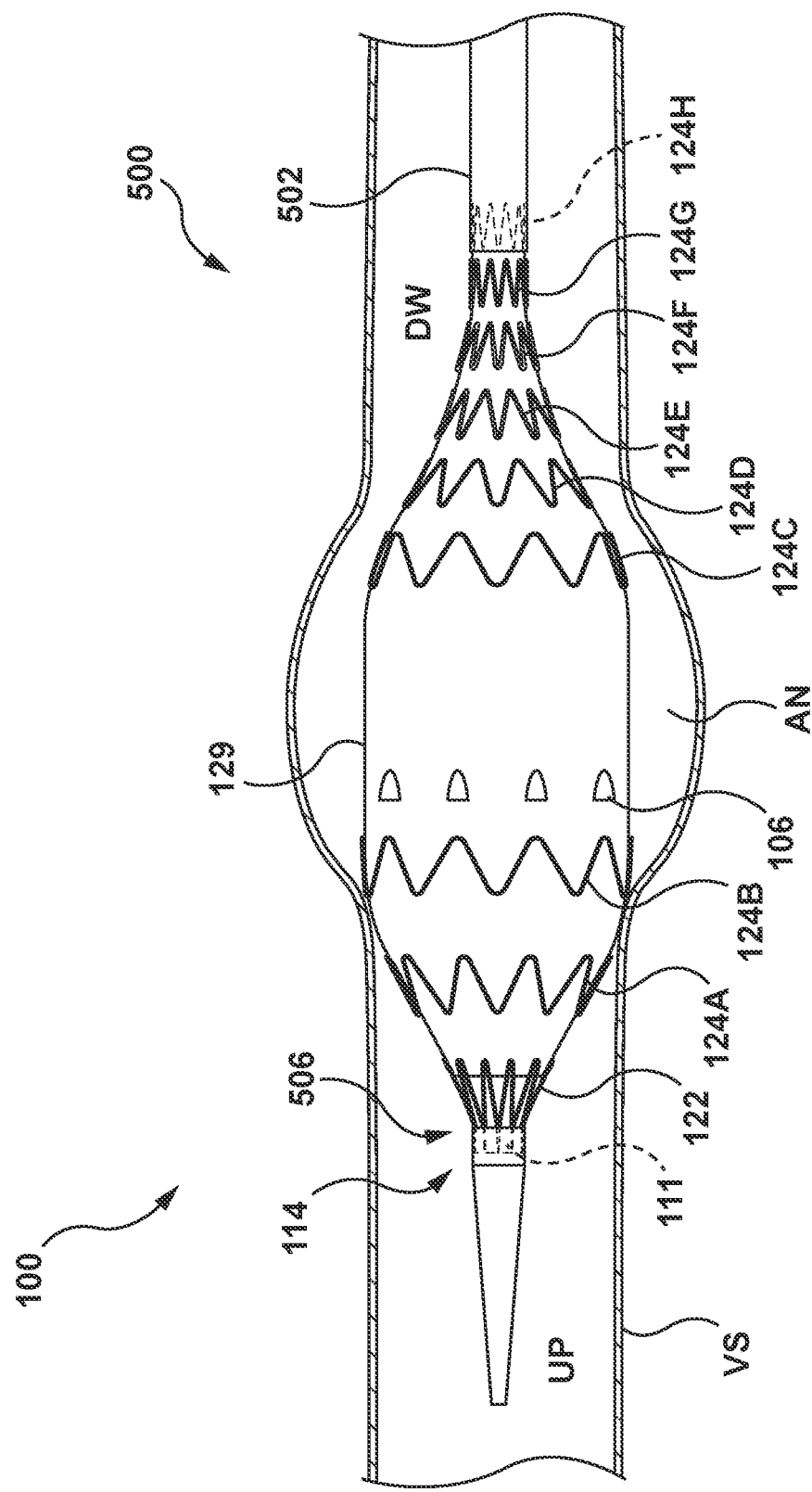
FIG. 6 depicts an illustration of a side view of the stent-graft prosthesis of FIG. 1 in situ, in a partially expanded configuration.
Figure 7:
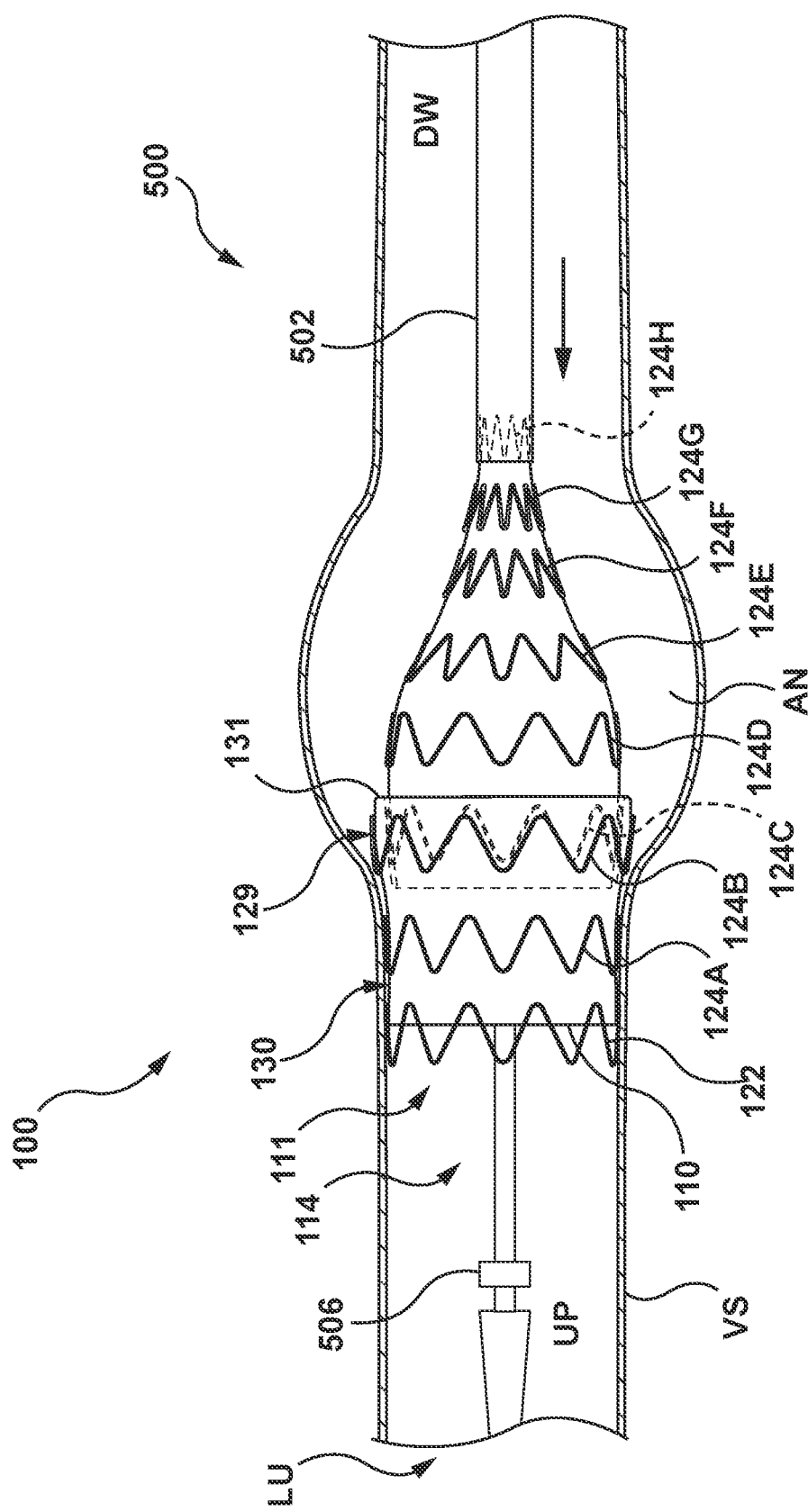
FIG. 7 depicts an illustration of a side view of the stent-graft prosthesis of FIG. 1 in situ, with a portion of the stent-graft prosthesis being folded to block ports of the stent-graft prosthesis, according to an embodiment hereof.

The blood flow explained above is at the stage of deployment shown in FIG. 4. As the outer sheath 502 continues to be retracted to release the stent-graft prosthesis 100, the blood flow from the upstream side UP to the downstream side DW of the stent-graft prosthesis 100 through the ports 106 is maintained, as shown in FIGS. 5 and 6. However, at a certain stage of deployment, prior to final deployment, the ports 106 must be closed such that blood flow through the ports 106 is stopped. Otherwise, after full deployment, blood flow would continue into the aneurysm AN through the ports 106, thereby defeating the purpose of the stent-graft prosthesis 100. In the embodiment of FIGS. 1-9, the ports 106 are closed by folding the unsupported graft portion 129 at a fold 131 such that unsupported graft portion 129 and the ports 106 fold under the body stent 124B, and the body stent 124C is positioned under the body stent 124B, to prevent blood from escaping the graft lumen 114 through the ports 106. As shown in FIG. 7, the delivery system 500 can be pushed distally such that the graft material 102 folds, most likely at a position just distal of the body stent 124B, i.e., in the unsupported graft portion 129. As shown in FIG. 7, the unsupported graft portion 129 downstream of the fold 131 and the third body stent 124C are relocated within the second body stent 124B such that the stent-graft prosthesis 100 is in a folded configuration. As would be evident to those skilled in the art, although the fold 131 is shown immediately downstream of the body stent 124B, this is not meant to be limiting. Further, the third body stent 124C need not extend within the second body stent 124B. Instead, in other embodiments, the unsupported graft portion 129 may be fold such that the third body stent 124C is located adjacent to the second body stent 124B.

Figure 8:
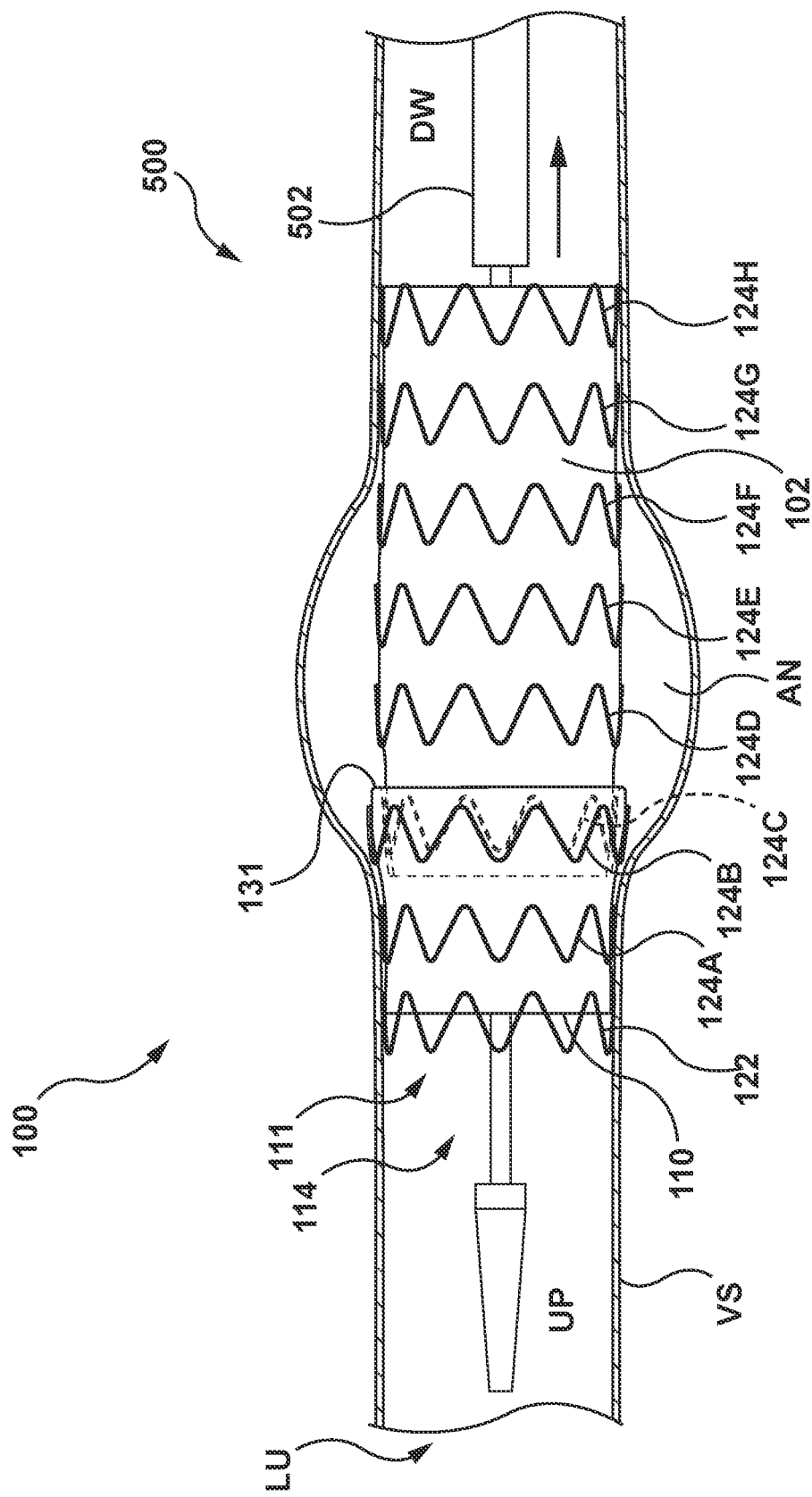
FIG. 8 depicts an illustration of a side view of the stent-graft prosthesis of FIG. 1 in situ, in a radially expanded, deployed configuration.
Figure 9:
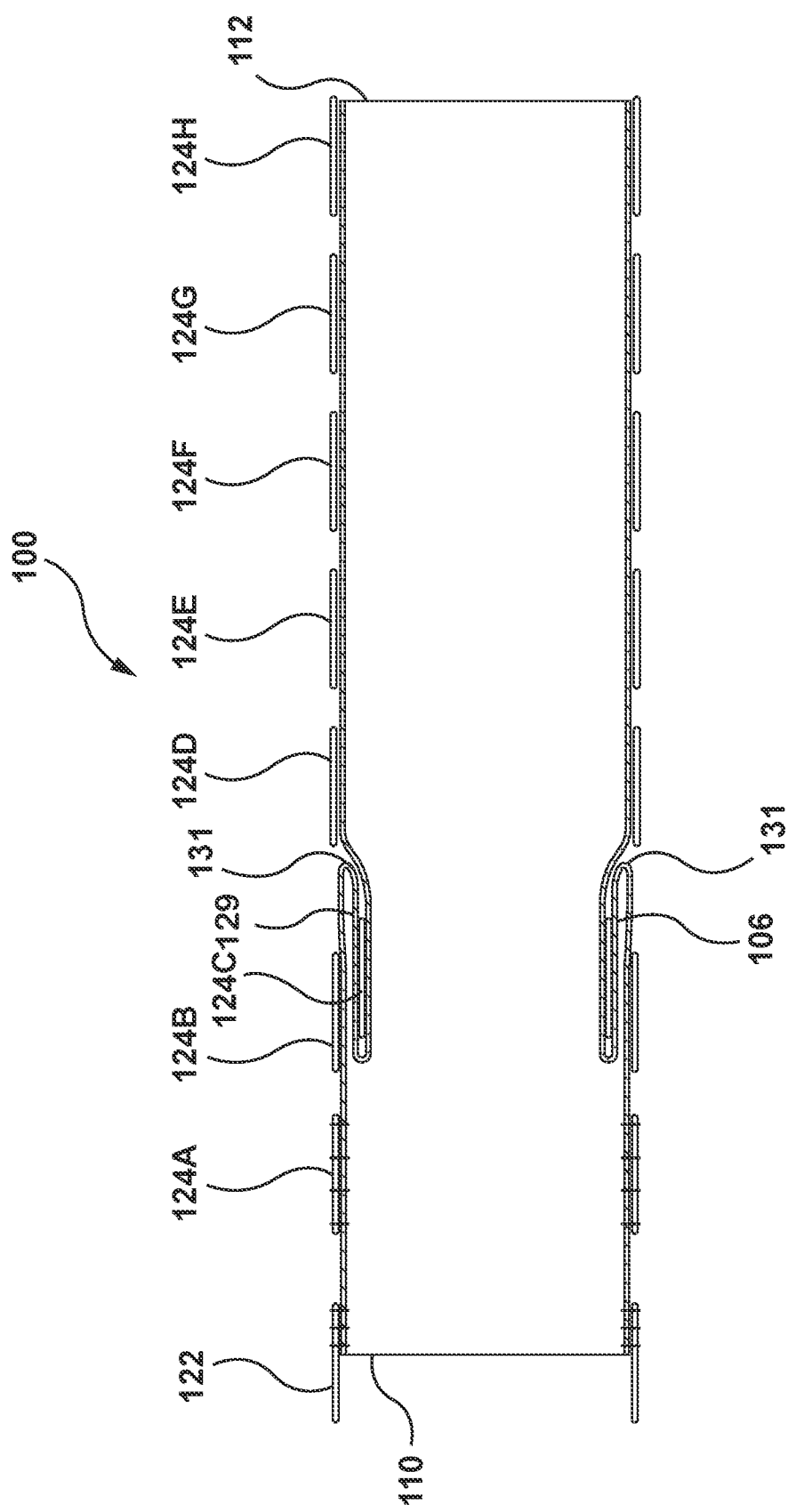
FIG. 9 depicts an illustration of a longitudinal cross-section view of the stent-graft prosthesis of FIG. 1 in the radially expanded, deployed configuration.

With the unsupported graft portion 129 folded such that the ports 106 are blocked, the outer sheath 502 may continue to be retracted to expose the remainder of the body stents 124 and enable the body stents 124 to self-expand, as shown in FIG. 8. The delivery system 500 may then be removed from the patient, leaving the stent-graft prosthesis 100 deployed in the vessel VS, with the ports 106 blocked so that blood may flow only through the graft lumen 114 from an upstream side of the stent-graft prosthesis 100 to a downstream side of the stent-graft prosthesis 100. FIG. 9 shows a cross-section view of the stent-graft prosthesis 100 as deployed, i.e., with the unsupported graft portion 129 folded to block the ports 106, with the vessel removed for clarity.

FIGS. 10-18 illustrate a stent-graft prosthesis 200 according to embodiments hereof. Similar to the embodiment of FIGS. 1-9, the stent-graft prosthesis 200 includes a graft material 202, a frame 204, and openings or ports 206 extending from an inner surface 218 to an outer surface 220 of the graft material 202. The stent-graft prosthesis 200 has a radially compressed configuration for delivery, a radially expanded configuration when deployed, and a partially expanded configuration when transitioning between the radially compressed and the radially expanded configurations. When the stent-graft prosthesis 200 is in the radially expanded configuration at a desired treatment location, the stent-graft prosthesis 200 is configured to bypass a vessel abnormality such as an aneurysm within a body vessel. While described herein as configured to bypass an aneurysm, such as an abdominal aortic aneurysm, this is by way of example and not limitation, and the stent-graft prosthesis 200 may be configured to support/bypass other vessel abnormalities such as, but not limited to dissections and transections.

The graft material 202 is of a generally tubular shape having a central longitudinal axis $L_A$, a first end or edge 210, a second end or edge 212, and a graft lumen or central passage 214 extending from the first end 210 to the second end 212. The graft material 202 has a longitudinal length 216, which may vary based upon the application. The first end 210 of the graft material 202 may be referred to as a proximal or an upstream end or edge of the graft material 202. In the embodiment shown, the first, proximal or upstream end or edge 211 of the stent-graft prosthesis 200 does not coincide with the first end 210 of the graft material 202 because a portion of the frame 204 extends past the first end 210 of the graft material 202. The second end 212 of the graft material 202 may be referred to as a distal or a downstream end or edge of the graft material 202. In the embodiment shown, the second end 212 of the graft material 202 is also a second, distal, or downstream end or edge 213 of the stent-graft prosthesis 200. For a stent-graft prosthesis for an abdominal aortic aneurysm delivered from the femoral artery, the proximal or upstream end 211 of the stent-graft prosthesis 200 is the end that may be coupled to a tip capture or retainer mechanism of a delivery system. The distal or downstream end 213 may also be coupled to a retainer or similar mechanism of the delivery system. The graft material 202 may be formed from any suitable graft material, for example and not way of limitation, the graft material 202 may be formed from a low-porosity woven or knit polyester, DACRON material, expanded polytetrafluoroethylene, polyurethane, silicone, or other suitable materials. In another embodiment, the graft material could also be a natural material such as pericardium or another membranous tissue such as intestinal submucosa.

Figure 10:
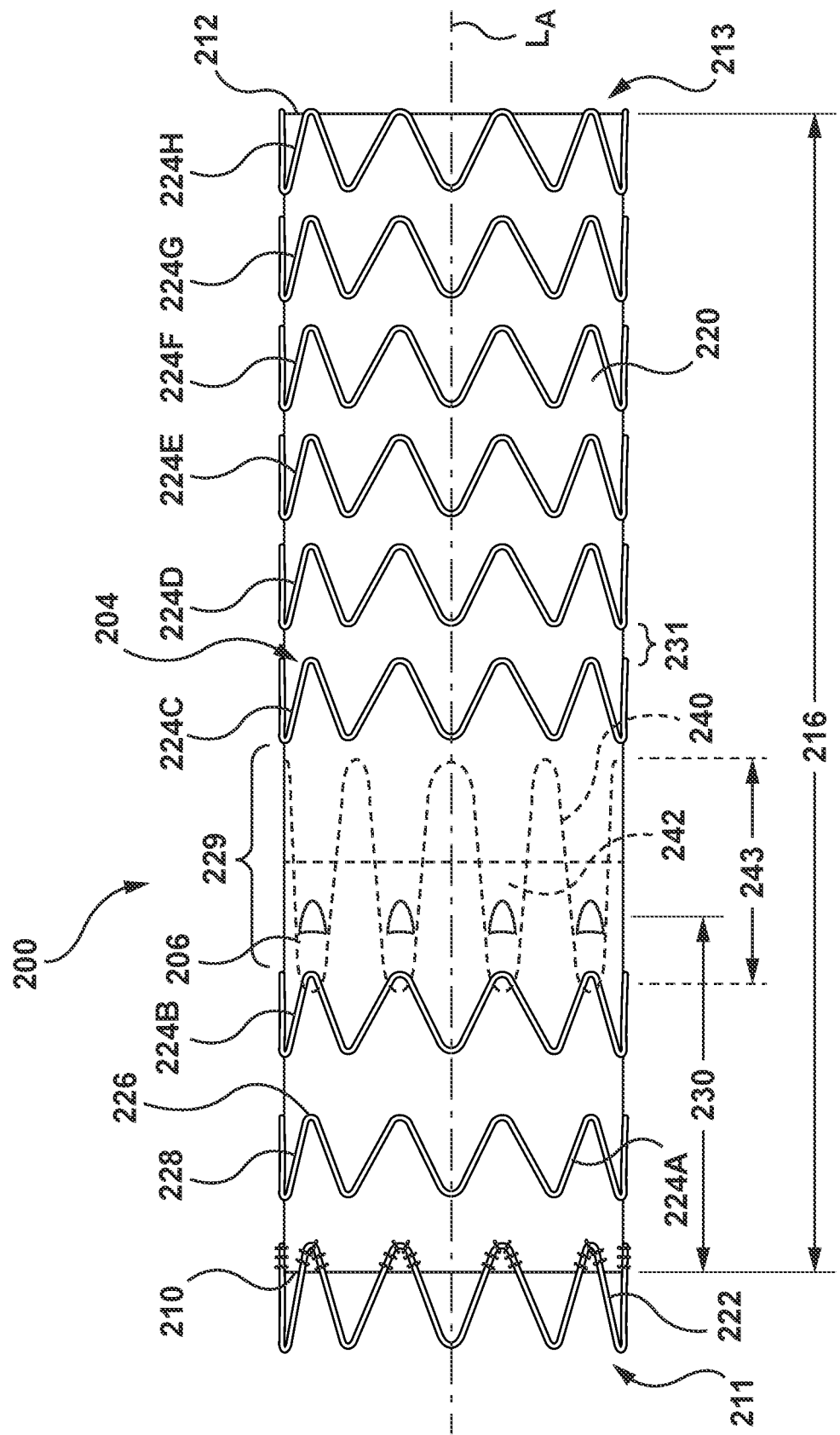
FIG. 10 depicts a schematic side view illustration of a stent-graft prosthesis in a radially expanded configuration according to another embodiment hereof.

Similar to the embodiment of FIGS. 1-9, in the embodiment of FIGS. 10-18, the frame 204 of the stent-graft prosthesis 200 includes a sealing or seal stent 222 and a plurality of body stents 224. The frame 204 is configured to support the graft material 202. The seal stent 222 and the body stents 224 may also be referred to as frame members. The seal stent 222 and each of the body stents 224 of the frame 204 are coupled to the graft material 202. In the embodiment illustrated in FIG. 10, the stent-graft prosthesis 200 is shown in the radially expanded configuration and includes one (1) seal stent 222 adjacent to the first end 210, and seven (7) body stents 224A-224G axially or longitudinally spaced between the first end 210 and the second end 212 of the graft material 202. Although shown with seven (7) body stents 224, it will be understood that the stent-graft prosthesis 200 may include more or fewer body stents 224 depending upon the desired length 216 of the stent-graft prosthesis 200 and/or the intended application. Further, the stent-graft prosthesis 200 includes an internal port closing stent 240 with graft material 242 disposed on portions thereof to close the ports 206 during deployment. In the embodiment of FIGS. 10-18, manipulation of the delivery system to fold the stent-graft prosthesis is not needed, as explained in more detail below. The seal stent 222, each of the body stents 224, and the port closing stent 240 are self-expanding and each includes a radially compressed state, a partially expanded state, and a radially expanded state. Accordingly, the seal stent 222, each of the body stents 224, and the port closing stent 240 are constructed from self-expanding materials as described previously. The seal stent 222, each of the body stents 224, and the port closing stent 240 may be sinusoidal patterned rings including a plurality of crowns or bends 226 and a plurality of struts or straight segments 228 with each crown 226 being formed between a pair of adjacent struts 228. While the seal stent 222 and the body stents 224 are shown in FIG. 10 as having a similar sinusoidal pattern, it will be understood that the seal stent 222 and the body stents 224 may have different patterns or configurations. The seal stent 222 and the body stents 224 are coupled to the graft material 102 by stitches or sutures 225 (see FIG. 11), or other suitable methods. In the embodiment of FIGS. 10-18, the seal stent 222 and the body stents 224 are coupled to the outer surface 220 of the graft material 202, and the port closing stent 240 is coupled to the inner surface 218 of the graft material 202, as explained in more detail below. However, the seal stent 222 and the body stents 224 alternatively may be coupled to the inner surface 218 of the graft material 202. When the stent-graft prosthesis 200 is used for treating an aneurysm, the seal stent 222 is configured with sufficient radial spring force and flexibility to conformingly engage the stent-graft prosthesis 200 with the body lumen inner wall, to avoid excessive leakage, and to prevent pressurization of the aneurysm, i.e., to provide a leak-resistant seal.

As briefly explained above, in the embodiment of FIG. 10, the proximal end 211 of the stent-graft prosthesis 200 has an open-web configuration in which the endmost crowns 226 of the seal stent 222 extend proximal of the first end 210 of the graft material 202, as shown in FIG. 10. As viewed in FIG. 10, the stent-graft prosthesis 200 includes a closed-web configuration at the distal end 213, with the endmost crowns 226 of the distal-most body stent 224H covered or lined by the material graft 202, i.e., they do not extend outside of or beyond the second end 212 of the graft material 202. In other embodiments hereof (not shown), the first end 211 and second end 213 of the stent-graft prosthesis 200 may both be an open-web configuration, may both be a closed-web configuration, or the first end 211 may be a closed-web configuration and the second end 213 may be an open-web configuration.

The plurality of ports 206 are configured to permit blood flow to escape the graft lumen 214 of the graft material 202 when the stent-graft prosthesis 200 is in the partially expanded configuration, as explained in more detail below. Accordingly, when the stent-graft prosthesis 200 is in the partially expanded configuration, the ports 206 are configured to relieve pressure associated with pulsatile blood flow on the stent-graft prosthesis 200 during implantation within a body vessel. The partially expanded configuration, as used herein, means that a portion or portions of the stent-graft prosthesis 200 are in a radially compressed state, portions of the stent-graft prosthesis 200 are in a partially expanded state, and portions of the stent-graft prosthesis 200 may be in a radially expanded state, as will be described below. As shown in FIG. 10, the ports 206 are located at the distal crowns 226 of the second body stent 224B. However, this is not meant to be limiting, and the ports 206 can be located elsewhere. Further, the number and size of the ports 206 can be selected to provide the proper amount of blood flow out of the graft lumen 214 during deployment of the stent-graft prosthesis 200. In embodiments, the ports 206 are evenly distributed around the circumference of the stent-graft prosthesis 200. In the embodiment shown, the ports 206 are disposed at the same the longitudinal location along the graft material 202. In other words, each of the ports 206 is located a distance 230 from the first end 210 of the graft material 202. However, this is not meant to be limiting, and the ports 206 may be located at different longitudinal locations. Further, the ports 206 in the embodiment shown may be described as a single row of ports 206. However, this is also not meant to be limiting, and multiple rows of ports 206 are contemplated. Further, the ports 206 need not be located after the second body stent 224B. Instead, the ports 206 may be located longitudinally to enable blood flow therethrough until the stent-graft prosthesis 200 is sufficiently deployed such that the stent-graft prosthesis 200 will hold its position in the vessel. The ports 206 may be openings through the graft material, as shown in FIG. 2A. In other embodiments, such as shown in FIG. 2B, the ports may include a mesh covering disposed over the port. The mesh covering includes openings of sufficient size to permit blood flow therethrough. The mesh covering may cover an outer surface of the graft material, an inner surface of the graft material, or both inner and outer surfaces of the graft material.

In the embodiment shown in FIGS. 10-18, the ports 206 are closed by the port closing stent 240 when the stent-graft prosthesis 200 is fully radially expanded such that blood flow into the aneurysm is prevented. In the embodiment shown, the third body stent 224C is spaced farther from the second body stent 224B than the other body stents 224 are spaced from an adjacent body stent 224. Thus, for example, a length 229 between the second body stent 224B and the third body stent 224C is longer than a length 231 between the third body stent 224C and the fourth body stent 224D. This additional length between the second body stent 224B and the third body stent 224C, combined with a longer length of the port closing stent 240, enables the ports 206 to remain open as more of the stent-graft prosthesis 200 is released from the outer shaft of the delivery device as explained in more detail below. In an embodiment, the length 229 is in the range of about 4 mm to about 40 mm, or about 10 mm to about 30 mm, or about 15 mm to about 25 mm. Further, in embodiments, a length 243 of the port closing stent 240 is in the range of 8 mm to about 30 mm, or about 10 mm to about 25 mm, or about 15 mm to about 20 mm. In some embodiments, the port closing stent 240 is at least as long as each of the body stents 224, or longer.

Figure 12:
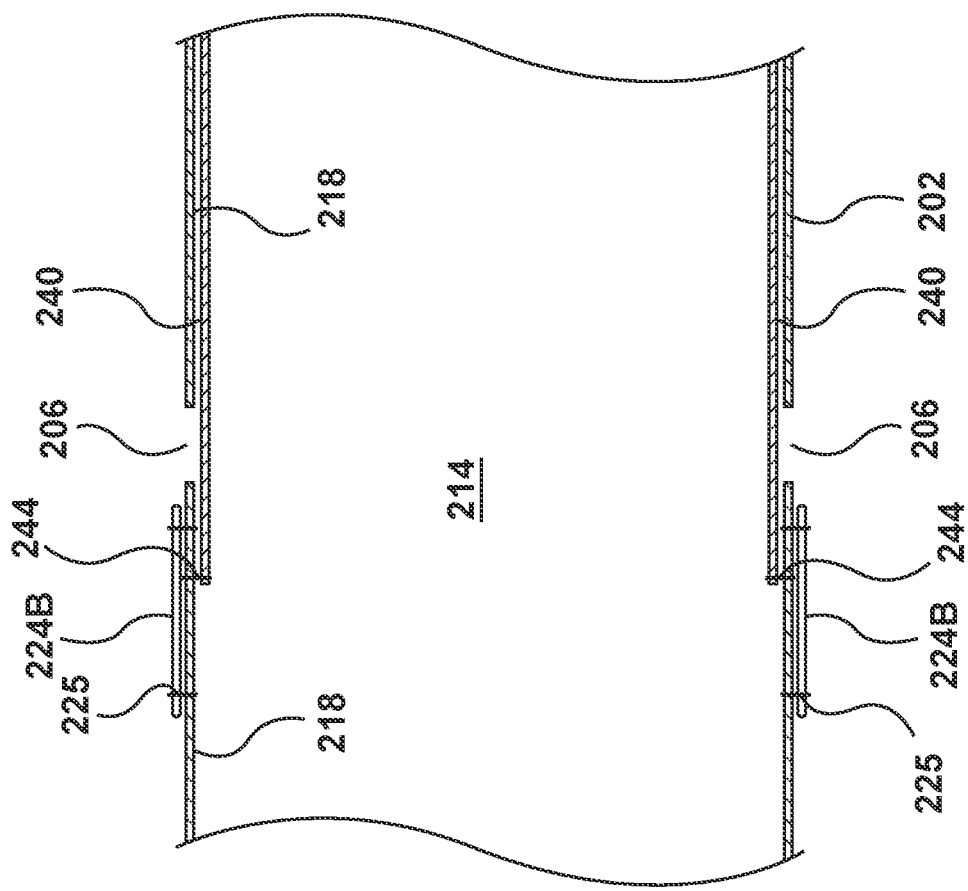
FIG. 12 depicts a schematic cross-section illustration of a portion of the stent-graft prosthesis of FIG. 10 according to embodiments hereof.
Figure 11:
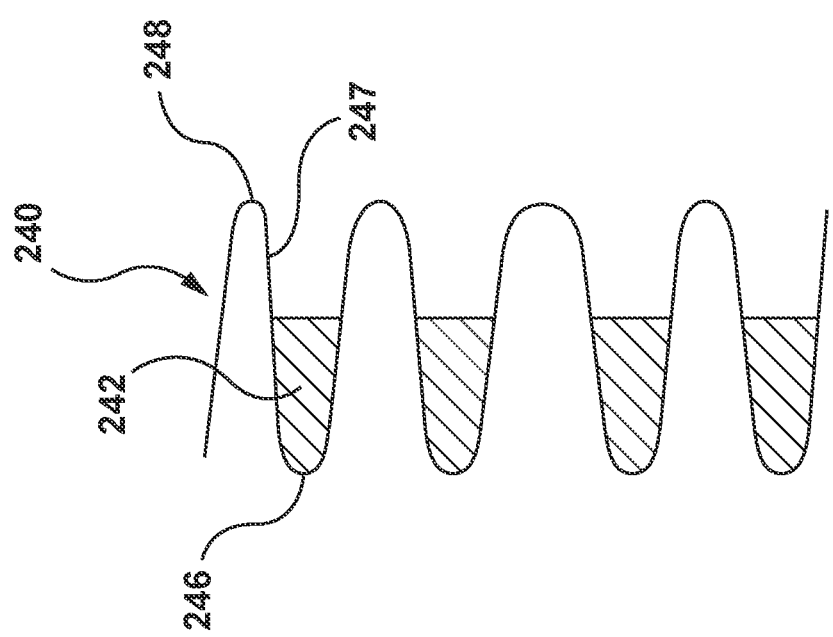
FIG. 11 depicts a schematic illustration of a port closing stent of the stent-graft prosthesis of FIG. 10 according to embodiments hereof.
Figure 13:
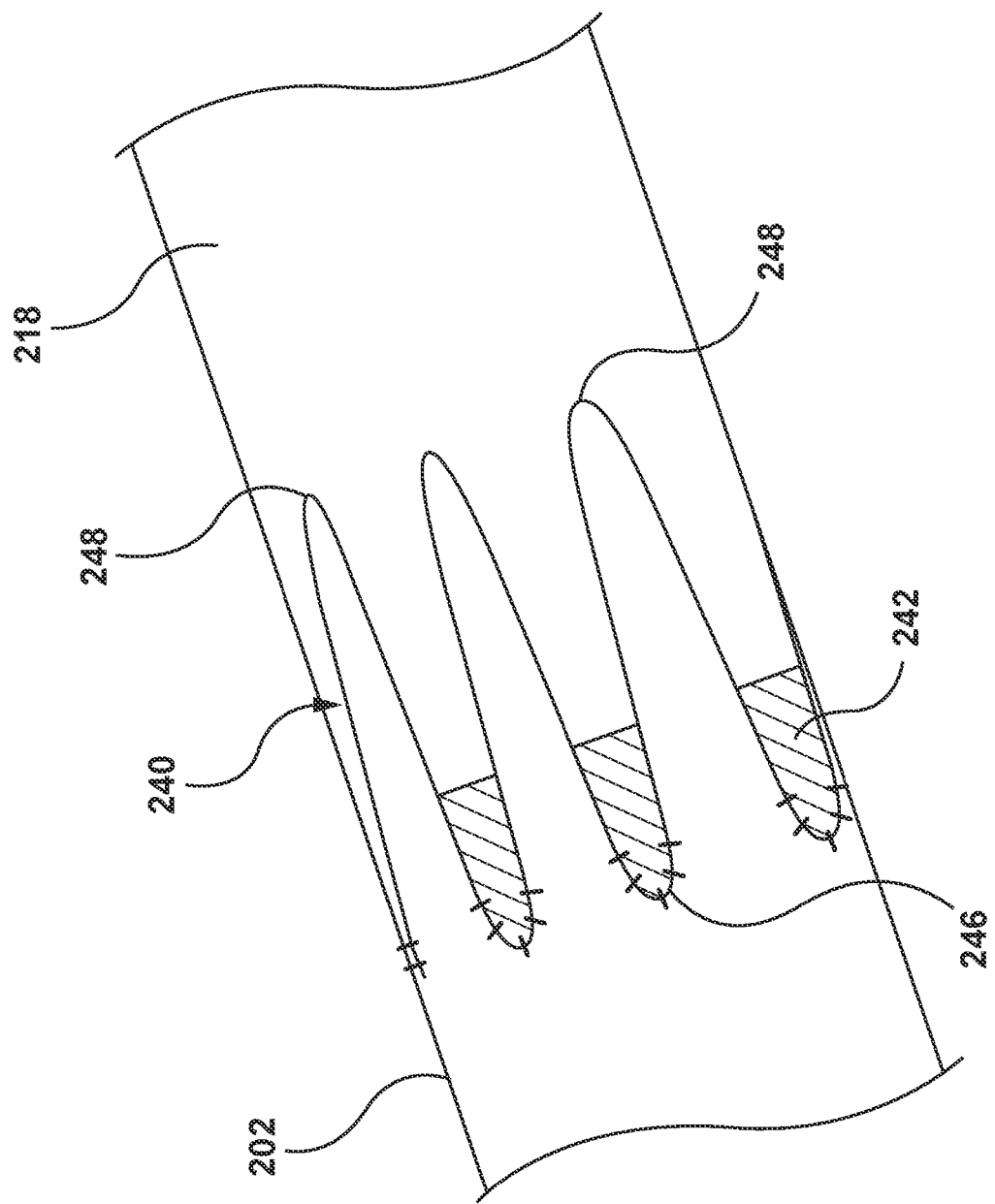
FIG. 13 depicts a perspective illustration of a portion of an interior of the stent-graft prosthesis of FIG. 10 according to embodiments hereof.

The port closing stent 240 is coupled to the inner surface 218 of the graft material 202. As shown in FIGS. 12-13, a proximal or upstream portion of the port closing stent 240 is attached to the inner surface 218 of the graft material 202, but a distal or downstream portion of the port closing stent 240 is not attached to the graft material 202. In the embodiment shown, the upstream crowns 246 of the port closing stent 240 are attached to the inner surface 218 of the graft material 202 using sutures, stitches, or other similar attachment means, with the downstream crowns 248 and the majority of the struts 247 of the port closing stent 240 unattached to the graft material 202. Further, an upstream or proximal blocking portion of the port closing stent 240 includes a graft material 242 attached thereto. As explained in more detail below, when the port closing stent 240 is released from the delivery device, the port closing stent 240 expands against the inner surface 218 of the graft material 202 such that the graft material 242 attached to the port closing stent 240 blocks the ports 206, thereby preventing blood flow from exiting the graft lumen 214 through the ports 206.

The operation of the stent-graft prosthesis 200 will now be explained with reference to FIGS. 14-18, some of which are sectional cutaway views of a vessel illustrating the delivery, positioning and deployment of the stent-graft prosthesis 200 at the site of a vessel abnormality, which in FIGS. 14-18 is an aneurysm. However, this is by way of example and not limitation and embodiments of the stent-graft prosthesis 200 may be utilized with other vessel abnormalities including, but not limited to dissections and transections.

Figure 14:
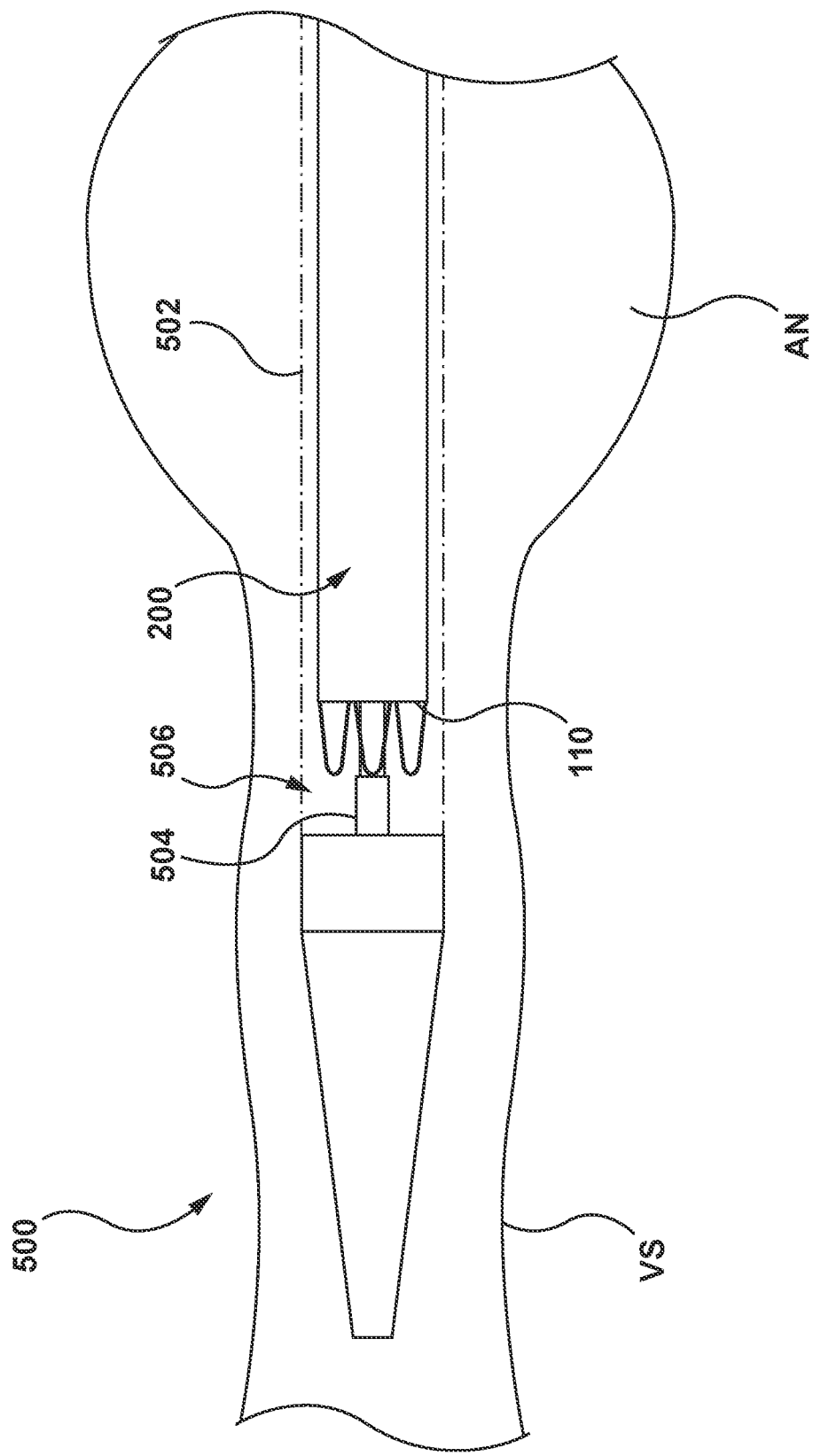
FIG. 14 depicts an illustration of a side view of the stent-graft prosthesis of FIG. 10 in situ, wherein the stent-graft prosthesis is disposed on a distal portion of a delivery system in a radially compressed configuration, according to embodiments hereof.

Referring now to FIG. 14, the stent-graft prosthesis 200 is disposed on a distal portion of the delivery system 500 in the radially compressed configuration. As described above, the delivery system 500 includes at least the outer sheath 502 and the inner shaft 504 having the tip capture mechanism 506 mounted thereon. The proximal end 211 of the stent-graft prosthesis 200 may be releasably coupled to the tip capture mechanism 506. The stent-graft prosthesis 200 is mounted on the inner shaft 504 and the outer sheath 502 encapsulates, covers, or restrains the stent-graft prosthesis 200 in the radially compressed configuration for delivery thereof. The delivery system 500 is advanced to a desired treatment location of an aneurysm AN in a vessel VS. In embodiments hereof, the delivery system 500 may be similar to the Captiva Delivery System, manufactured by Medtronic Vascular, Inc. of Santa Rosa, California, or a delivery system as described in U.S. Patent Application Publication No. 2009/0276027 to Glynn, or U.S. Pat. No. 8,882,828 to Kinkade et al., each of which is incorporated by reference herein in its entirety.

Figure 15:
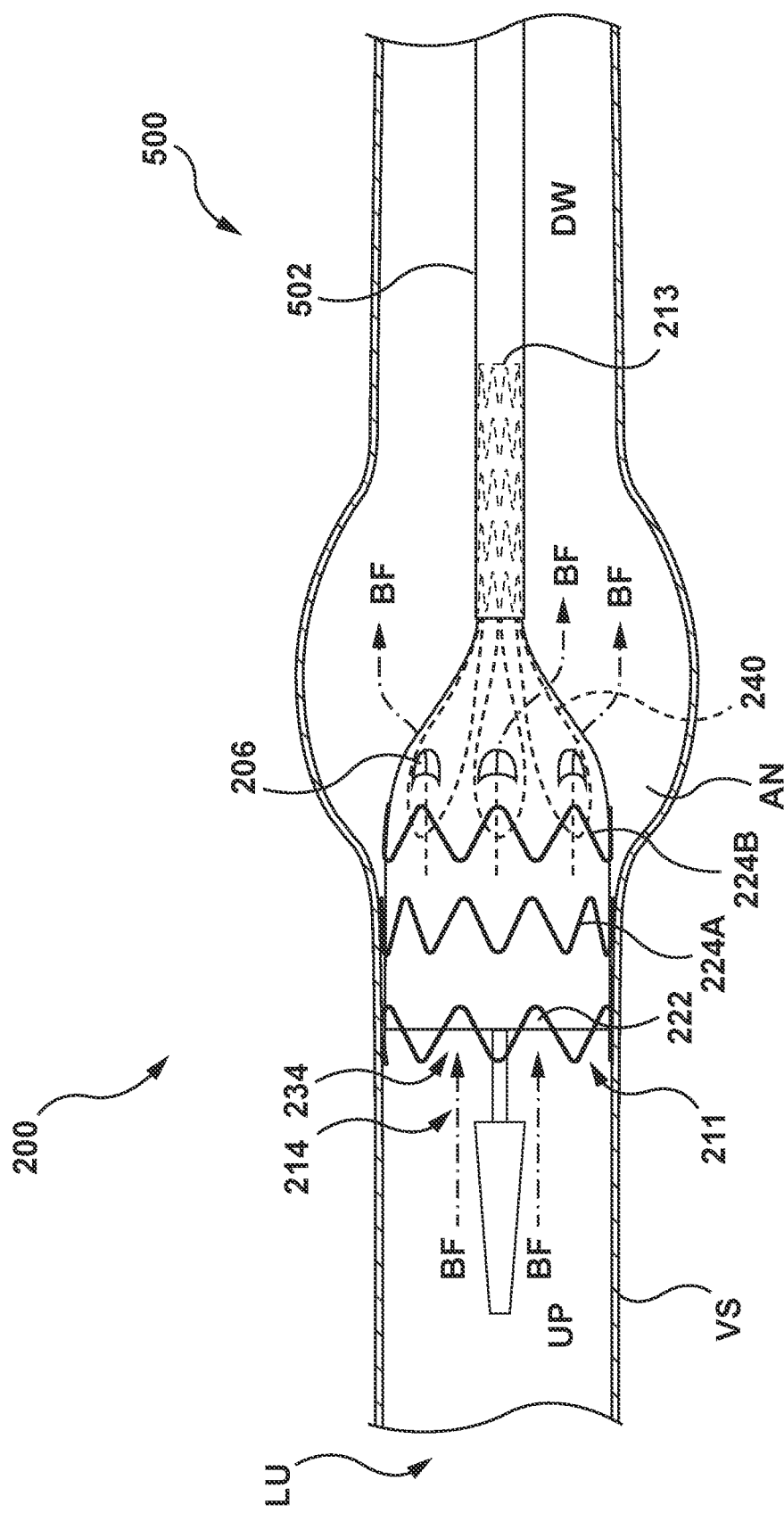
FIG. 15 depicts an illustration of a side view of the stent-graft prosthesis of FIG. 10 in situ, in a partially expanded configuration, according to embodiments hereof.

Once the stent-graft prosthesis 200 is at the desired treatment location within the vessel VS, the stent-graft prosthesis 200 may be deployed from the delivery system 500. The outer sheath 502 of the delivery system 500 is retracted to release a portion the stent-graft prosthesis 200. The released portion of the stent-graft prosthesis 200 radially expands within the vessel VS and the stent-graft prosthesis 200 transitions to a partially expanded configuration, as shown in FIG. 15. In the embodiment shown in FIG. 15, as opposed to the embodiment shown in FIG. 4, the first end 211 of the stent graft prosthesis 200 is released from the tip capture mechanism 506. This is not meant to be limiting, and in any of the embodiments described herein the first end of any of the stent-graft prostheses described herein may stay restrained within the tip capture mechanism 506 until most or all of the remainder of the stent-graft prosthesis is released form the outer sheath 502, as shown in FIG. 4, or the first end may be released prior to the ports being closed such that the seal stent is radially expanded against the vessel wall, as shown in FIG. 15, thereby providing stability to the stent-graft prosthesis prior to closing of the ports.

Still referring to FIG. 15, at least the distal end 213 of the stent graft prosthesis 200 is restrained in the radially compressed state by the outer sheath 502. At the deployment stage shown in FIG. 15, the portion of the stent-graft prosthesis 200 restrained by the outer sheath 502 also includes the body stents 224C-224G. As can be seen in FIG. 15, a portion of the stent-graft prosthesis 200, extending from the seal stent 222 to the second body stent 224B is in the radially expanded configuration. Between the radially expanded portion and the portion restrained within the outer sheath 502 is a tapered portion tapering from the radially expanded configuration to the radially compressed configuration restrained within the outer sheath 502.

Figure 16:
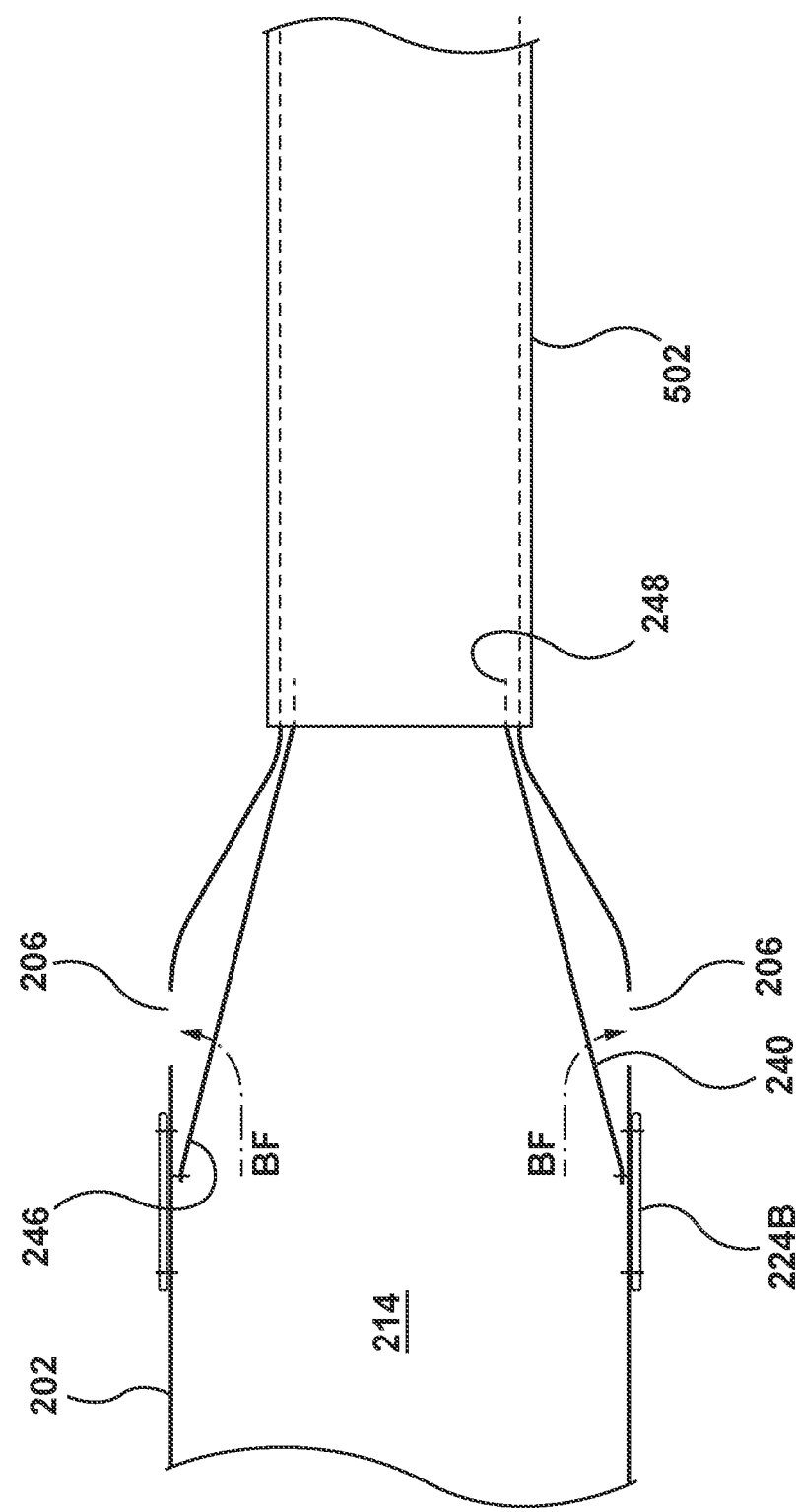
FIG. 16 depicts an illustration of a cross-sectional view of a portion of the stent-graft prosthesis of FIG. 10 in a partially expanded configuration, according to embodiments hereof.

When in the partially expanded configuration of FIG. 15, and prior to thereto, the stent-graft prosthesis 200 occludes the lumen LU of the vessel VS. Thus, blood flow does not pass within the lumen LU of the vessel VS around the outside of the stent-graft prosthesis 200. Thus, blood flow enters within the graft lumen 214 of the graft material 202 via an opening 234 at the first end 210 of the graft material 202. However, as explained above, blood entering the graft lumen 214 of the graft material 202 in a conventional stent-graft prosthesis would not be able to escape the graft lumen 214, thereby possibly resulting in "windsocking" or a "windsock" effect. However, with the stent-graft prosthesis 200, blood that enters the graft lumen 214 of the graft material 202 can exit through the ports 206, as shown in FIGS. 15 and 16. Thus, blood from an upstream side UP of the stent-graft prosthesis 200 is permitted to travel into the stent-graft prosthesis 200, out of the stent-graft prosthesis 200 through the ports 206 to the downstream side DW of the stent-graft prosthesis 200. More precisely, blood on the upstream side UP of the stent-graft prosthesis 200 enters the graft lumen 214 of the stent-graft prosthesis 200 through the opening 234 at the first end 210 of the graft material 202, travels through the graft lumen 214 of the stent-graft prosthesis 200, and exits to the downstream side DW of the stent-graft prosthesis 200 through the ports 206. The exit of the blood flow through the ports 206 relieves pressure build-up within the stent-graft prosthesis 200. Further, the flow of blood through the ports 206 from the upstream side UP to the downstream side DW of the stent-graft prosthesis 200 provides blood supply to vessels downstream of the stent-graft prosthesis 200. When the pressure associated with the pulsatile blood flow is relieved by the ports 206 during deployment of the stent-graft prosthesis 200, the stent-graft prosthesis 200 can be more precisely positioned. In addition, the position of the stent-graft prosthesis 2100 can be more easily maintained during deployment of the stent-graft prosthesis 200.

Referring to FIG. 16, blood flow around the port closing stent 240 at the deployment stage shown in FIG. 15 is explained. As shown, at this stage of deployment, the second body stent 224B and the ports 206 have been released from the outer sheath 502 of the delivery system 500, enabling the second body stent 224B to radially expand, thereby radially expanding the graft material 202 and the ports 206 located adjacent to the second body stent 224B. As shown in FIGS. 15-16, the proximal or upstream crowns 246 of the port closing stent 240 are attached to the inner surface 218 of the graft material 202 upstream of the ports 206. However, at this stage of deployment, the downstream crowns 248 of the port closing stent 240 remain radially constrained within the outer sheath 502 of the delivery system 500. Thus, the portion of the port closing stent 240 adjacent the ports 206 is not radially expanded against the inner surface 218 of the graft material 202. Thus, blood can flow around the port closing stent 240 and the graft material 242 attached thereto, and exit the graft lumen 214 through the ports 206, as shown in FIG. 16.

Figure 17:
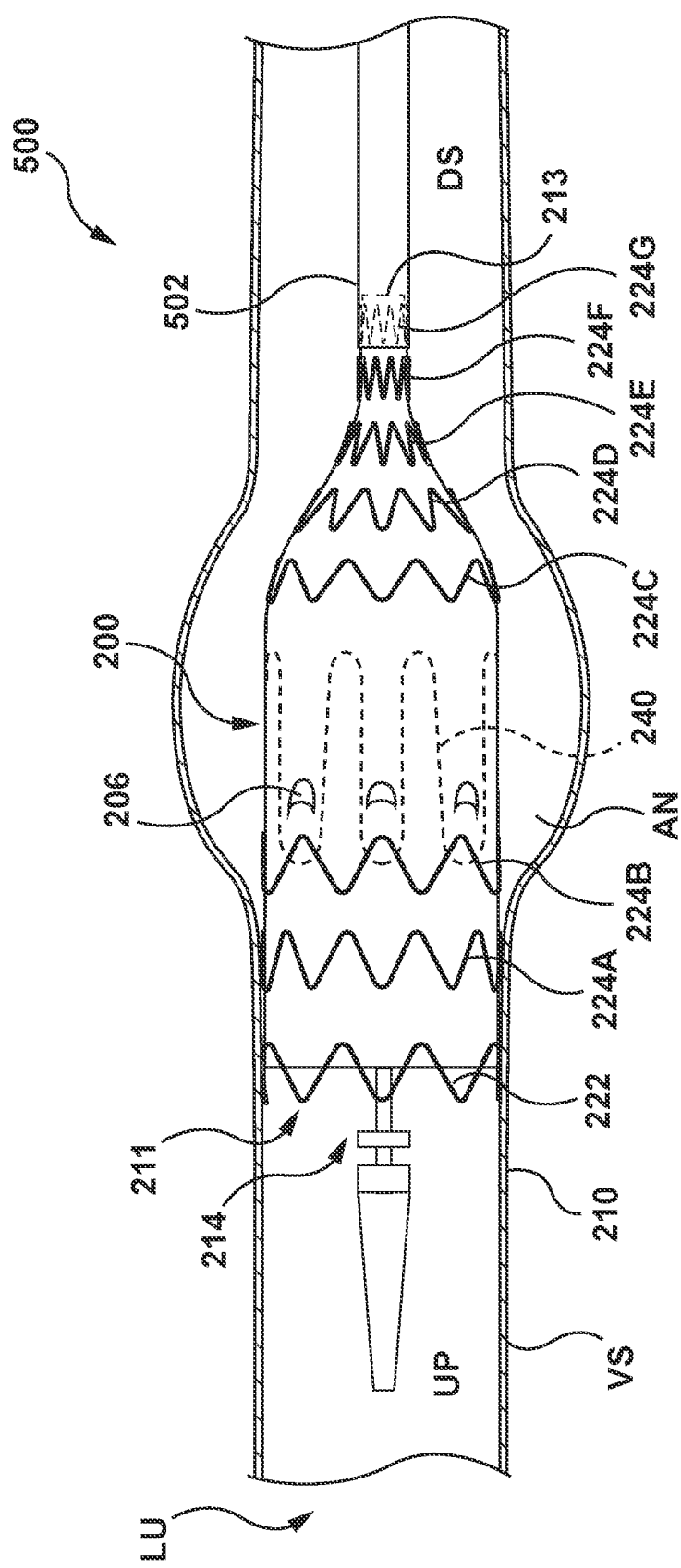
FIG. 17 depicts an illustration of a side view of the stent-graft prosthesis of FIG. 10 in situ, in a partially expanded configuration with the port closing stent radially expanded to close the ports thereof, according to embodiments hereof.

As the outer sheath 502 of the delivery system 500 is further retracted from around the stent-graft prosthesis 200, the downstream crowns 248 of the port closing stent 240 are eventually released from the outer sheath 502, thereby enabling self-expansion of the port closing stent 240, as shown in FIG. 17. With the port closing stent 240 radially expanded, it presses against the inner surface 218 of the graft material 202. Further, the graft material 242 of the port closing stent 240 is pressed against the inner surface 218 of the graft material 202 at the location of the ports 206, thereby blocking the ports 206. In other words, the graft material 242 of the port closing stent 240 blocks flow from the graft lumen 214 through the ports 206.

Figure 18:
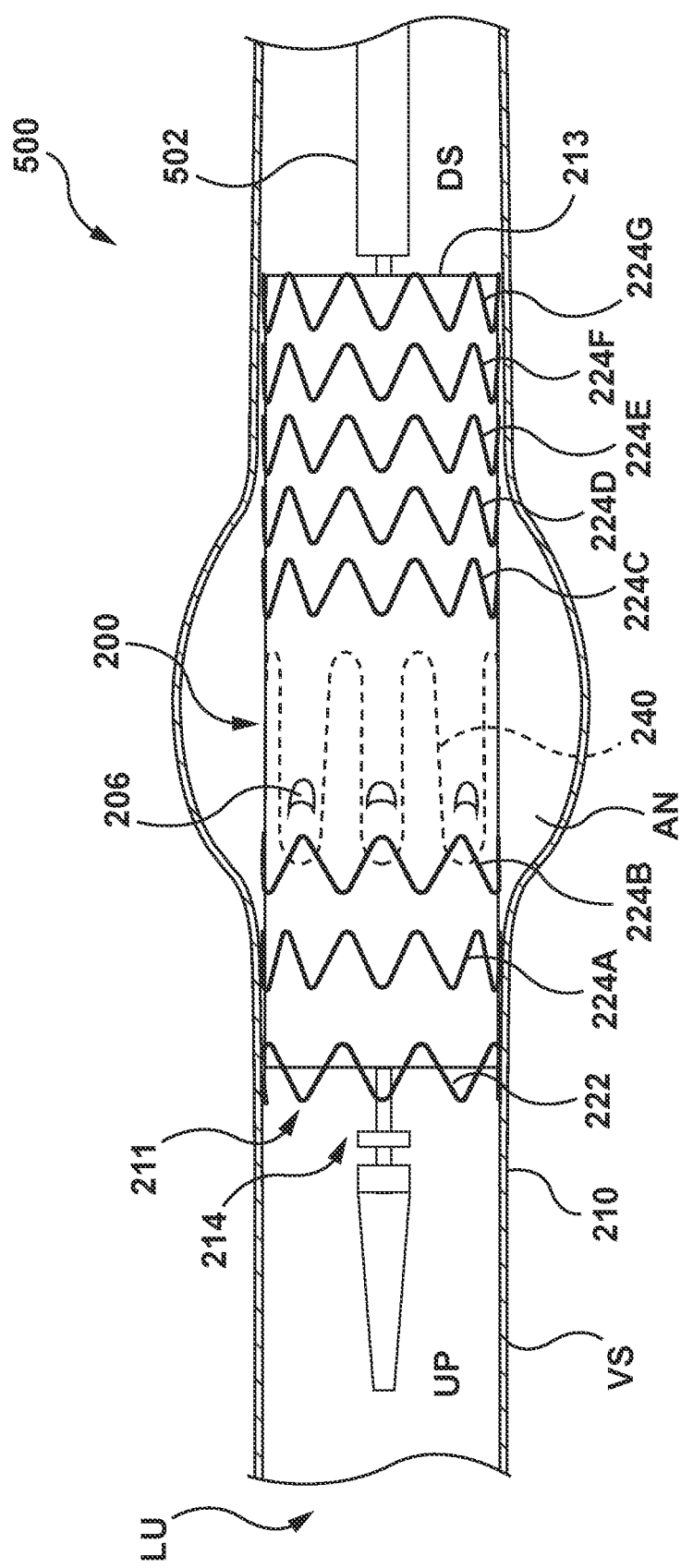
FIG. 18 depicts an illustration of a side view of the stent-graft prosthesis of FIG. 10 in situ, in a radially expanded, deployed configuration, according to embodiments hereof.

Final deployment of the stent-graft prosthesis 200 is achieved by retracting the outer sheath 502 to release the second end 213 of the stent-graft prosthesis 200, as shown in FIG. 18. With the stent-graft prosthesis 200 fully deployed, blood flow enters the opening 234 at the first end 211 of the stent-graft prosthesis 200, flows through the graft lumen 214, is prevented from exiting through the ports 206, and exits the graft lumen 214 through the opening at the second end 213 of the stent-graft prosthesis 200. The delivery system 500 may then be removed from the patient, leaving the stent-graft prosthesis 200 implanted such that blood flow bypasses the aneurysm AN.

Figure 19A:
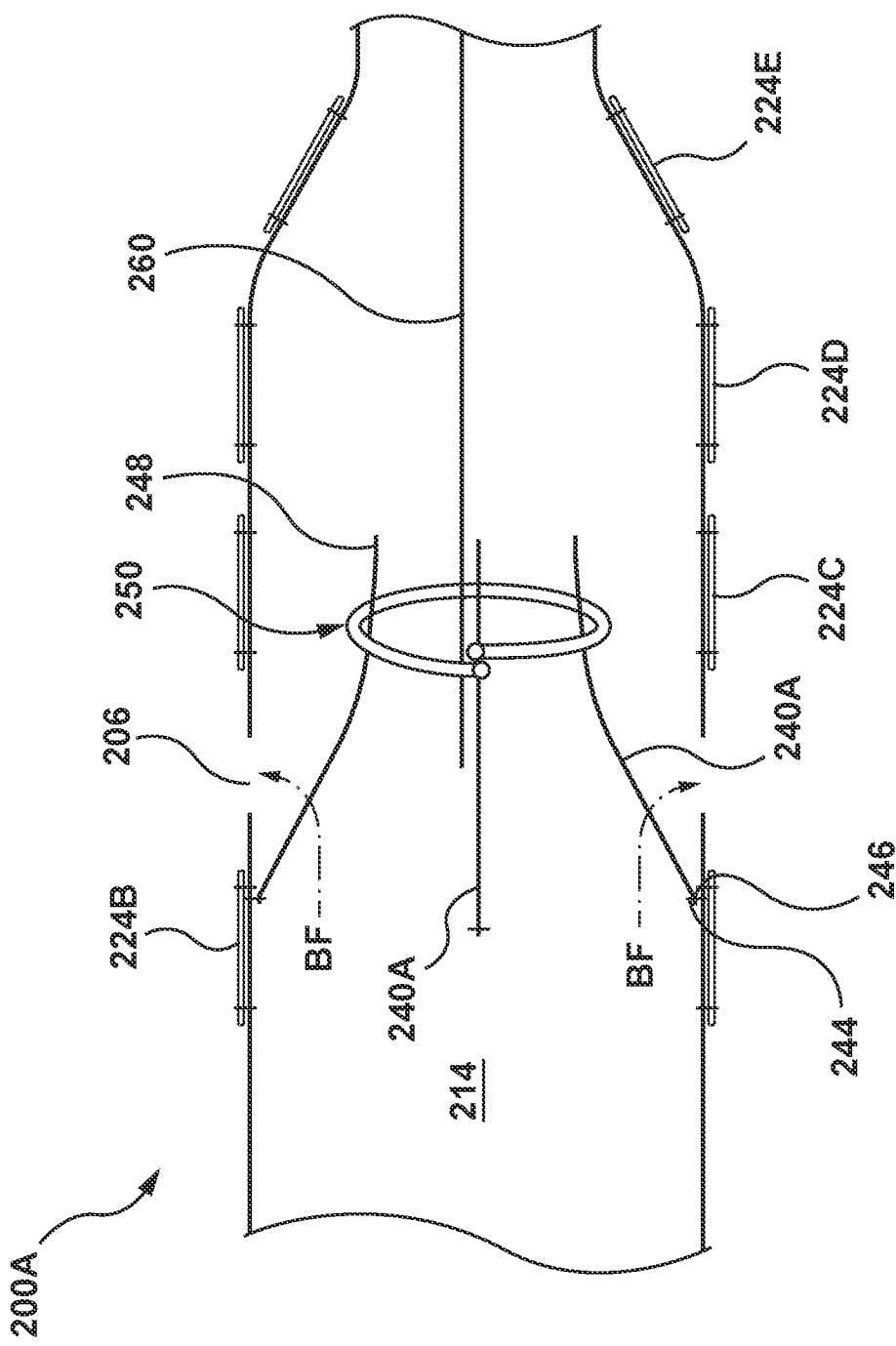
FIG. 19A depicts an illustration of a longitudinal cross-section view of a portion of the stent-graft prosthesis of FIG. 10 using circumferentially constraining sutures to radially compress a portion of a port closing stent, according to embodiments hereof.
Figure 19C:
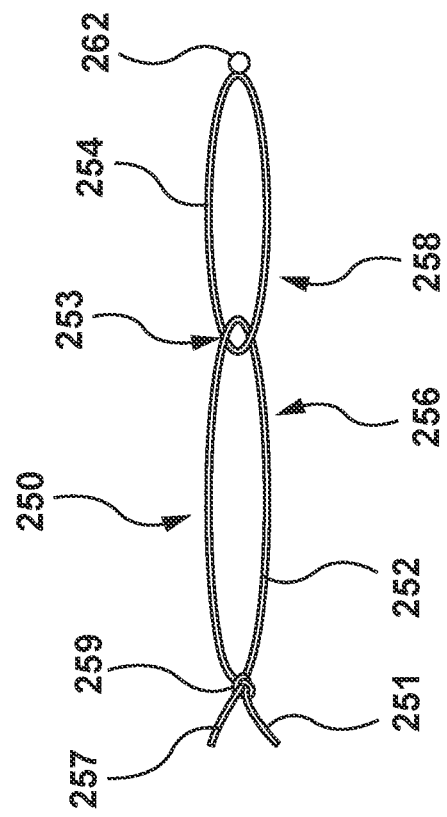
FIG. 19C depicts a schematic illustration of a circumferentially restraining suture, according to embodiments hereof.
Figure 19B:
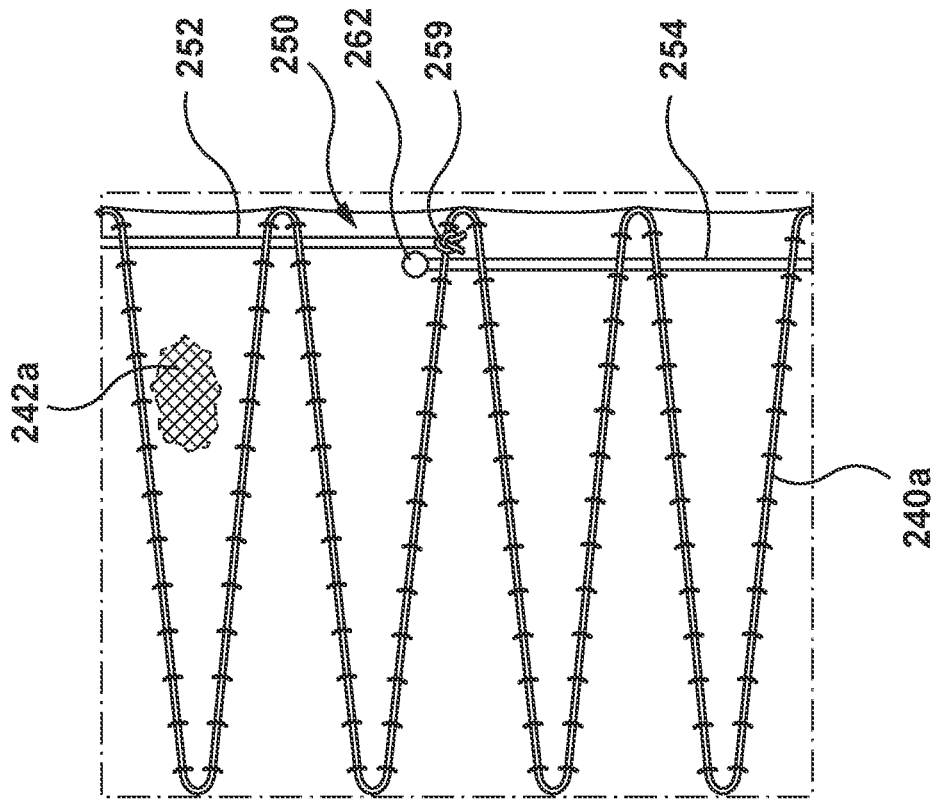
FIG. 19B depicts a schematic illustration of a circumferentially constraining suture of FIG. 19A coupled to a port closing stent, according to embodiments hereof.

FIGS. 19A-19C show an embodiment of a stent-graft prosthesis 200A that is similar to the stent-graft prosthesis 200 described above with respect to FIGS. 10-18. Therefore, the details of the stent-graft prosthesis 200A that are the same as the stent-graft prosthesis 200 will not be repeated here. Those skilled in the art will recognize that the details, alternatives, variations, etc. described above with respect to the stent-graft prosthesis 200 apply to the stent-graft prosthesis 200A.

The stent-graft prosthesis 200A shown in FIGS. 19A-19C includes a port closing stent 240A with graft material 242A attached thereto. As with the stent-graft prosthesis 200, the upstream crowns 246 of the port closing stent 240A of the stent-graft prosthesis 200A are attached to the inner surface 218 of the graft material 202 of the stent-graft prosthesis 200A, such as with sutures 244, and the downstream crowns 248 of the port closing stent 240A are not attached to the graft material 202. However, instead of the downstream crowns 248 being maintained in a radially compressed configuration by the outer sheath 502 of the delivery system 500, as described above, the downstream crowns 248 of the port closing stent 240A of the stent-graft prosthesis 200A are maintained in the radially compressed configuration by a circumferentially restraining suture 250 and a release or trigger wire 260. While reference is made herein to a restraining suture, this is not intended to be limiting, and the restraining suture may be replaced by any elongated member, such as a filament, cord, wire, or other long and flexible structure/material.

In an embodiment, the circumferentially constraining suture 250 is disposed around the port closing stent 240A. Although a single circumferentially constraining suture 250 is shown, those skilled in the art would recognize that more circumferentially constraining sutures 250 may be utilized depending on several factors, such as the length of the port closing stent 240A. In an embodiment the circumferentially constraining suture 250 and the trigger wire 260 are as described in U.S. Patent Publication No. 2013/0289713, assigned to Medtronic Vascular, Inc., the contents of which are incorporated by reference herein. Briefly, in such an embodiment, as shown in FIGS. 19B and 19C, the circumferentially constraining suture 250 comprises a first thread or string 252 interlocked with a second thread or string 254 at an interlocking location 253. The first thread 252 is formed into a first thread loop 256 by having a first end 251 and a second end 257 of first thread 252 disposed adjacent to each other and tied to each other at a knot 259, as shown in FIG. 19C. Essentially, the first thread 252 is folded back at approximately a mid-point thereof to form a first thread loop 256. The first thread 252 has a thread length in the folded configuration that is less than the circumference of port closing stent 240A when expanded. Similarly, the second thread 256 is folded back at approximately a mid-point thereof to form a second thread loop 258, as shown in FIG. 19C. In an embodiment, ends of the second thread 254 disposed opposite the interlocking location 253 are tied or otherwise attached to a pull tab 262. The pull tab 262 as shown is a circular, donut shaped tab. However, those of ordinary skill in the art would recognize that other pull tabs may be used, or a large knot tied in the ends of the second thread 254 may function as a pull tab. Further, those of ordinary skill in the art would recognize that other ways of forming first and second threads with interlocked first and second thread loops may be used.

As explained in U.S. Patent Publication No. 2013/0289713, noted above, the first thread loop 256 is tied to a strut of the port closing stent 240A, as shown in FIG. 19B. The first thread loop 256 extends between port closing stent 240A and the graft material 242 attached thereto, and between sutures or stitches attaching the graft material 242 to the port closing stent 240A, thereby keeping first thread loop 256 from moving longitudinally port closing stent 240A. As further explained in U.S. Patent Publication No. 2013/0289713, the circumferentially constraining suture 250 functions to circumferentially constrain the port closing stent 240A by pulling on the pull tab 262, which pulls the second thread 254 and the attached first thread 252 around the circumference of the port closing stent 240A until the first thread loop 256 is adjacent the first and second ends 251, 257. Further, because first thread 252 is fixed to a port closing stent 240A, pulling the second thread 254 and first thread 252 along with it causes first thread 252 to circumferentially close or tighten or shrink the port closing stent 240A.

Next, the release or trigger wire 260 is inserted through first thread loop 256. Thus, when the pull tab 262 is released, the trigger wire 260 holds the distal crowns 248 of the port closing stent 240A in the radially compressed configuration by maintaining the first thread loop 256 in the configuration wherein it circumscribes the circumference of the port closing stent 240A at the distal crowns 248. The second thread 254 at this time can be removed, such as by cutting, and the trigger wire 250 will hold the distal crowns 248 of the port closing stent 240A in the radially compressed configuration.

While a specific embodiment of a circumferentially constraining suture has been described above, it is understood that this is not meant to be limiting, and other circumferentially constraining sutures or diameter reducing ties may be used to maintain the distal crowns 248 of the port closing stent 240A in the radially compressed configuration.

In operation, as described above with respect to FIGS. 14-16, the stent graft-prosthesis 200A with the distal crowns 248 of the port closing stent 240A circumferentially constrained in the radially compressed configuration, may be radially compressed into delivery system 500 and delivered to a treatment site. The outer sheath 502 of the delivery system 500 is proximally retracted to partially deploy the stent-graft prosthesis 200A, until the ports 206 are exposed. Because the distal crowns 248 of the port closing stent 240A are circumferentially restrained in the radially compressed configuration, blood can flow into the graft lumen 214 and out through the ports 206. At any time after the stent-graft prosthesis 200A has been sufficiently deployed that its position can be reliably maintained, the trigger wire 260 may be pulled, thereby releasing the circumferentially restraining suture 250, enabling the distal crowns 248 of the port closing stent 240A to radially expand. With the port closing stent 240A radially expanded, the graft material 242 of the port closing stent 240A covers the ports 206, thereby preventing blood flow from within the graft lumen 214 from exiting through the ports 206. The port closing stent 240A may be radially expanded at any time, as described above, but preferably is radially expanded prior to portions of the stent-graft prosthesis 200A downstream of the aneurysm AN being deployed, so as not to permit continued blood flow into the aneurysm AN with nowhere for the blood flow to escape, thereby possibly allowing for an undesirable build-up of pressure in the aneurysm.

Figure 20:
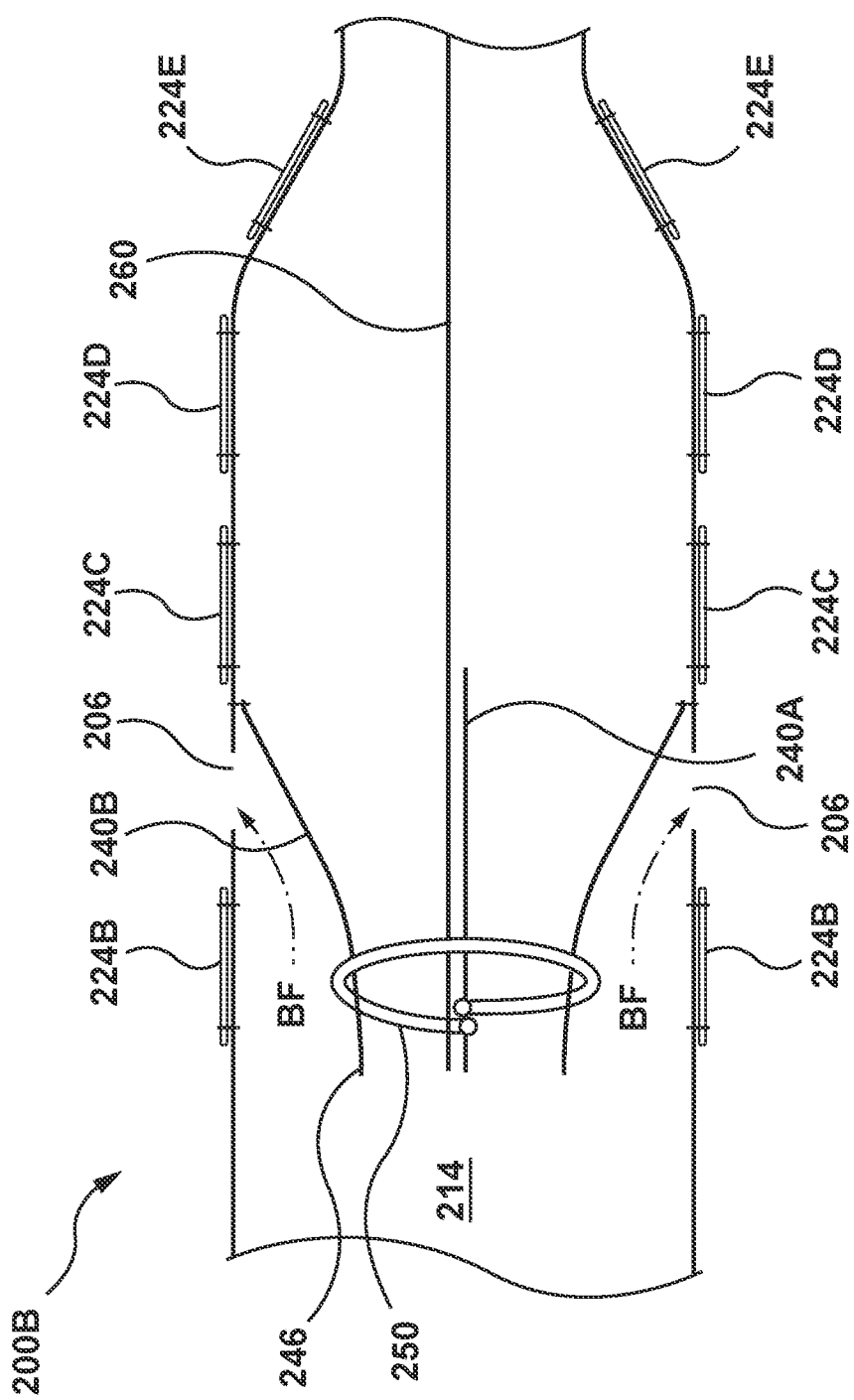
FIG. 20 depicts an illustration of a longitudinal cross-section view of a portion of the stent-graft prosthesis of FIG. 10 with another embodiment of a port closing stent using circumferentially constraining sutures to radially compress a portion of a port closing stent, according to embodiments hereof.

FIG. 20 shows an embodiment of a stent-graft prosthesis 200B that is similar to the stent-graft prosthesis 200 described above with respect to FIGS. 10-18 and the stent-graft prosthesis 200A described with respect to FIGS. 19A-19C. Therefore, the details of the stent-graft prosthesis 200B that are the same as the stent-graft prosthesis 200 and/or stent-graft prosthesis 200A will not be repeated here. Those skilled in the art will recognize that the details, alternatives, variations, etc. described above with respect to the stent-graft prostheses 200 and 200A apply to the stent-graft prosthesis 200B.

The stent-graft prosthesis 200B shown in FIG. 20 includes a port closing stent 240B with graft material (not shown) attached thereto. The stent graft prosthesis 200B is similar to the stent-graft prosthesis 200A in that a portion of the port closing stent 200B is maintained in a radially compressed configuration by a circumferentially restraining suture 250. However, the configuration of the stent-graft prosthesis 200B differs from the stent-graft prosthesis 200A in that the distal crowns 248 of the port closing stent 240B are attached to the graft material 202 and the proximal crowns 246 are not attached to the graft material 202. As would be understood, this is the opposite of the port closing stent 240A of the stent-graft prosthesis 200A of FIGS. 19A-19C, wherein the proximal crowns 246 are attached to the graft material 202 and the distal crowns 248 are unattached to the graft material 202.

In the embodiment of FIG. 20, with proximal crowns 248 radially constrained, the port closing stent 240B may act as a ramp to direct blood flow to the ports 206, as indicated by the arrows BF in FIG. 20.

Delivery and deployment of the stent-graft prosthesis 200B is the same as for the stent-graft prosthesis 200A. As described above with respect to FIGS. 14-16, the stent graft-prosthesis 200B with the proximal crowns 246 of the port closing stent 240B circumferentially constrained in the radially compressed configuration, may be radially compressed into the delivery system 500 and delivered to a treatment site. The outer sheath 502 of the delivery system 500 is proximally retracted to partially deploy the stent-graft prosthesis 200B, until the ports 206 are exposed. Because the proximal crowns 246 of the port closing stent 240B are circumferentially restrained in the radially compressed configuration, blood can flow into the graft lumen 214 and out through the ports 206. At any time after the stent-graft prosthesis 200B has been sufficiently deployed that its position can be reliably maintained, the trigger wire 260 may be pulled, thereby releasing the circumferentially restraining suture 250, enabling the proximal crowns 246 of the port closing stent 240B to radially expand. With the port closing stent 240B radially expanded, the graft material 242 of the port closing stent 240B covers the ports 206, thereby preventing blood flow from within the graft lumen 214 from exiting through the ports 206. The port closing stent 240B may be radially expanded at any time, as described above, but preferably is radially expanded prior to portions of the stent-graft prosthesis 200B downstream of the aneurysm AN being deployed, so as not to permit continued blood flow into the aneurysm AN with nowhere for the blood flow to escape, thereby possibly allowing for an undesirable build-up of pressure in the aneurysm.

Figure 21:
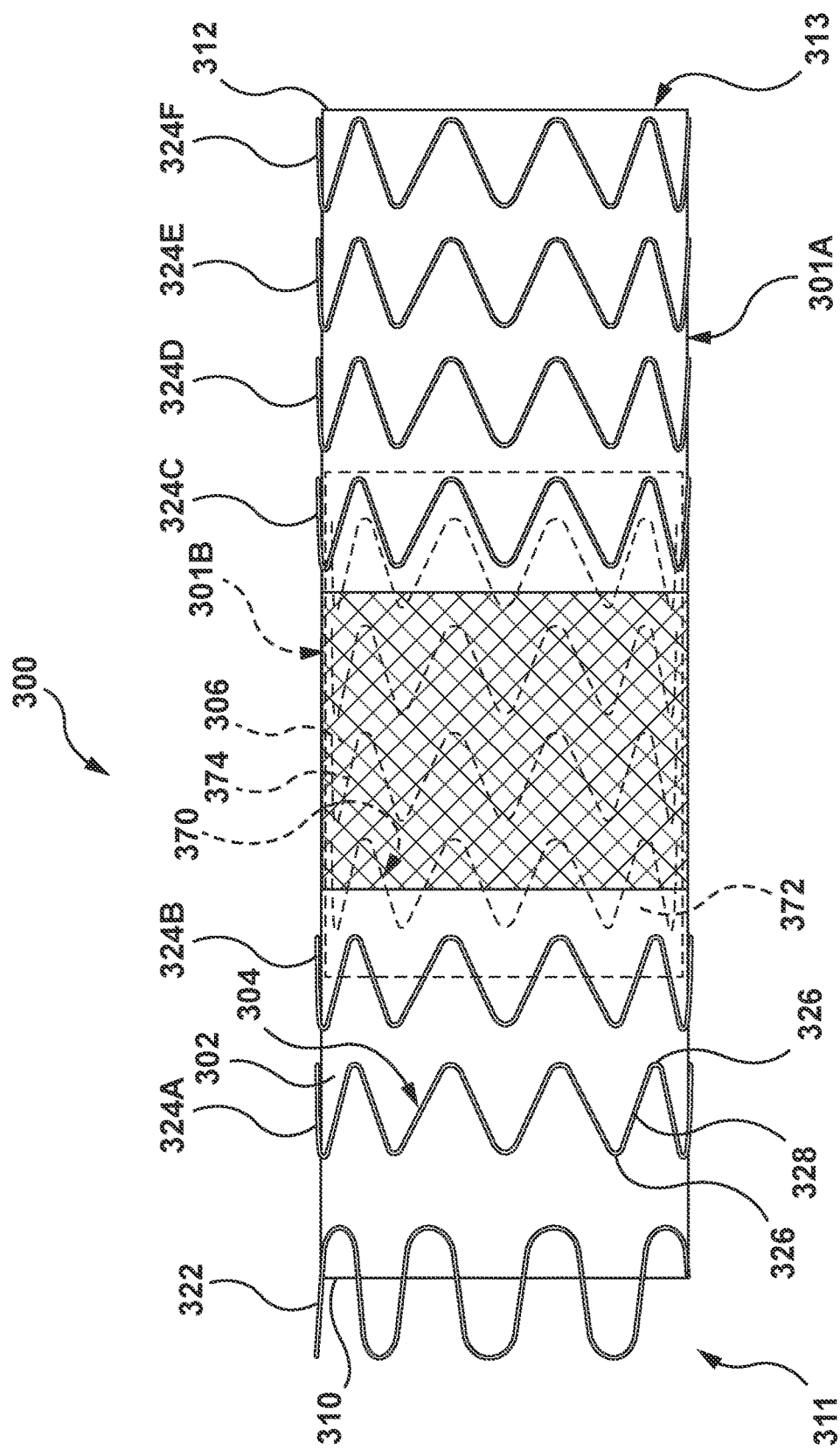
FIG. 21 depicts a schematic side view illustration of a stent-graft prosthesis in a radially expanded configuration according to another embodiment hereof.

FIGS. 21-26 show a stent-graft prosthesis 300 according to another embodiment hereof. The stent-graft prosthesis 300 includes an outer stent-graft 301A and an inner stent-graft 301B. The outer stent-graft 301A is similar to the stent-graft prostheses 100, 200 described above, in that it includes a graft material 302 and a frame 304. In the embodiment of FIG. 21, a mesh portion 306 of the graft material 302 may be a mesh with openings of sufficient size to enable blood flow therethrough. In an alternative embodiment, shown in FIG. 22, the outer stent-graft 301A may include a plurality of ports 306A, as described above with respect to FIGS. 1-20. The outer stent-graft 301A has a radially compressed configuration for delivery, a radially expanded configuration when deployed, and a partially expanded configuration when transitioning between the radially compressed and the radially expanded configurations. When the stent-graft prosthesis 300 is in the radially expanded configuration at a desired treatment location, the stent-graft prosthesis 300 is configured to bypass a vessel abnormality such as an aneurysm within a body vessel. While described herein as configured to bypass an aneurysm, such as an abdominal aortic aneurysm, this is by way of example and not limitation, and the stent-graft prosthesis 300 may be configured to support/bypass other vessel abnormalities such as, but not limited to dissections and transections.

Figure 22:
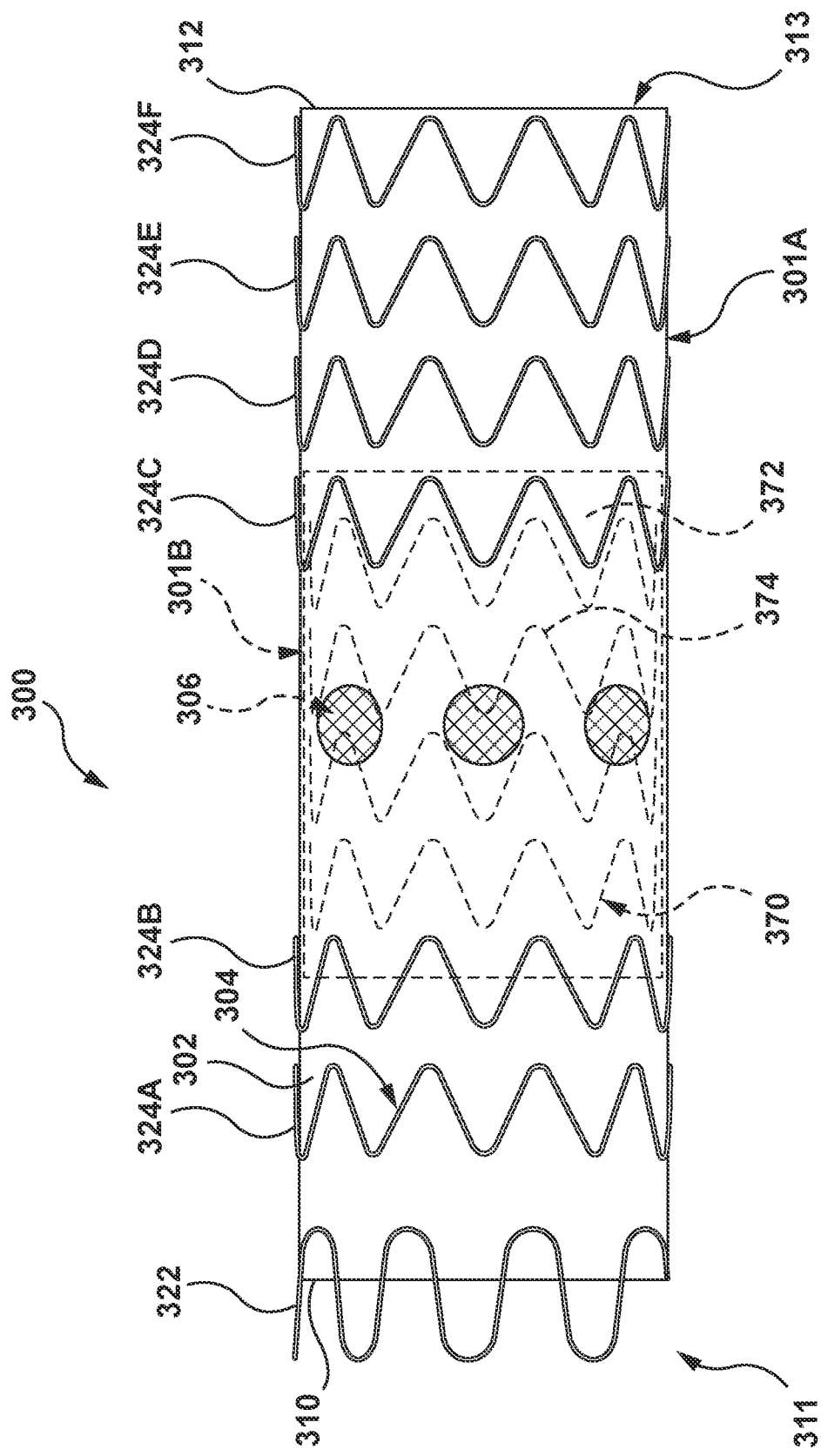
FIG. 22 depicts a schematic side view illustration of a stent-graft prosthesis in a radially expanded configuration according to another embodiment hereof.

The graft material 302 is of a generally tubular shape having a central longitudinal axis $L_A$, a first end or edge 310, a second end or edge 312, and a graft lumen or central passage 314 extending from the first end 310 to the second end 312. The graft material 302 has a longitudinal length which may vary based upon the application. The stent-graft prosthesis 300 includes a first, proximal or upstream end or edge 311 and a second, distal, or downstream end or edge 313. The graft material 302 may be formed from any suitable graft material, for example and not way of limitation, the graft material 202 may be formed from a low-porosity woven or knit polyester, DACRON material, expanded polytetrafluoroethylene, polyurethane, silicone, or other suitable materials. In another embodiment, the graft material could also be a natural material such as pericardium or another membranous tissue such as intestinal submucosa. The mesh portion 306 of the graft material may be formed of stainless steel, Nitinol, titanium, non-absorbable synthetic polymers and other composites, and other materials suitable for the purposes described herein. In the embodiment of FIG. 22, the ports 306A may be the same material as the mesh portion 306, or may be openings or holes, as described above with respect to FIGS. 1-20.

Similar to the embodiments of FIGS. 1-20, the frame 304 of the outer stent-graft 301A includes a sealing or seal stent 322 and a plurality of body stents 324. The seal stent 322 and body stents 324 may also be referred to as frame members. The frame 304 is configured to support the graft material 302. The seal stent 322 and each of the body stents 324 of the frame 304 are coupled to the graft material 302. In the embodiment illustrated in FIGS. 20-21, the stent-graft prosthesis 300 is shown in the radially expanded configuration and includes one (1) seal stent 322 adjacent to the first end 310, and six (6) body stents 324A-324F axially or longitudinally spaced between the first end 310 and the second end 312 of the graft material 302. Although shown with six (6) body stents 324, it will be understood that the outer stent-graft 301A may include more or fewer body stents 324 depending upon the desired length 316 of the outer stent-graft 301A and/or the intended application. Further, although the outer stent-graft 301A is shown without body stents attached in the mesh portion 306 of FIG. 21 or the area surrounding ports 306 in FIG. 22, this is not meant to be limiting, and body stents may be provided in these areas.

The inner stent-graft 301B is a conventional stent-graft in that it includes a frame 370 and graft material 372. The frame 370 may comprise a plurality of stents 374 and/or a helical stent (not shown), as known to those skilled in the art. The graft material 372 may be the graft materials described above with respect to the graft material 302. As explained in more detail below, the inner stent-graft 301B is used to prevent blood flow from the graft lumen 314 of from exiting the mesh portion/ports 306 of the outer stent-graft 301A. Therefore, the graft material 372 is a material that does not permit blood flow therethrough. The inner stent-graft 301B is delivered within the outer stent-graft 301A and remains in a radially compressed configuration until the outer stent-graft 301A has been sufficiently deployed to minimize the windsock effect, at which time the inner stent-graft 301B may be released such as to radially expand to block the mesh portion/ports 306 of the outer stent-graft 301A, as explained in more detail below. The inner stent-graft 301B may be maintained in a radially compressed configuration by a plurality of circumferentially constraining sutures 350, as explained above with respect to the embodiments of FIGS. 19A-19C and 20, other diameter reducing sutures/ties, or may be constrained within a shaft of a delivery system, as described below.

FIGS. 23, 24A, 24B, and 25 show the stent-graft prosthesis 300 of FIG. 21 being deployed at a treatment site, particularly an aneurysm AN. However, this is by way of example and not limitation and embodiments of the stent-graft prosthesis 300 may be utilized with other vessel abnormalities including, but not limited to, dissections and transections. Further, it is understood that this method applies equally to the variation of the stent-graft prosthesis 300 shown in FIG. 22.

Figure 23:
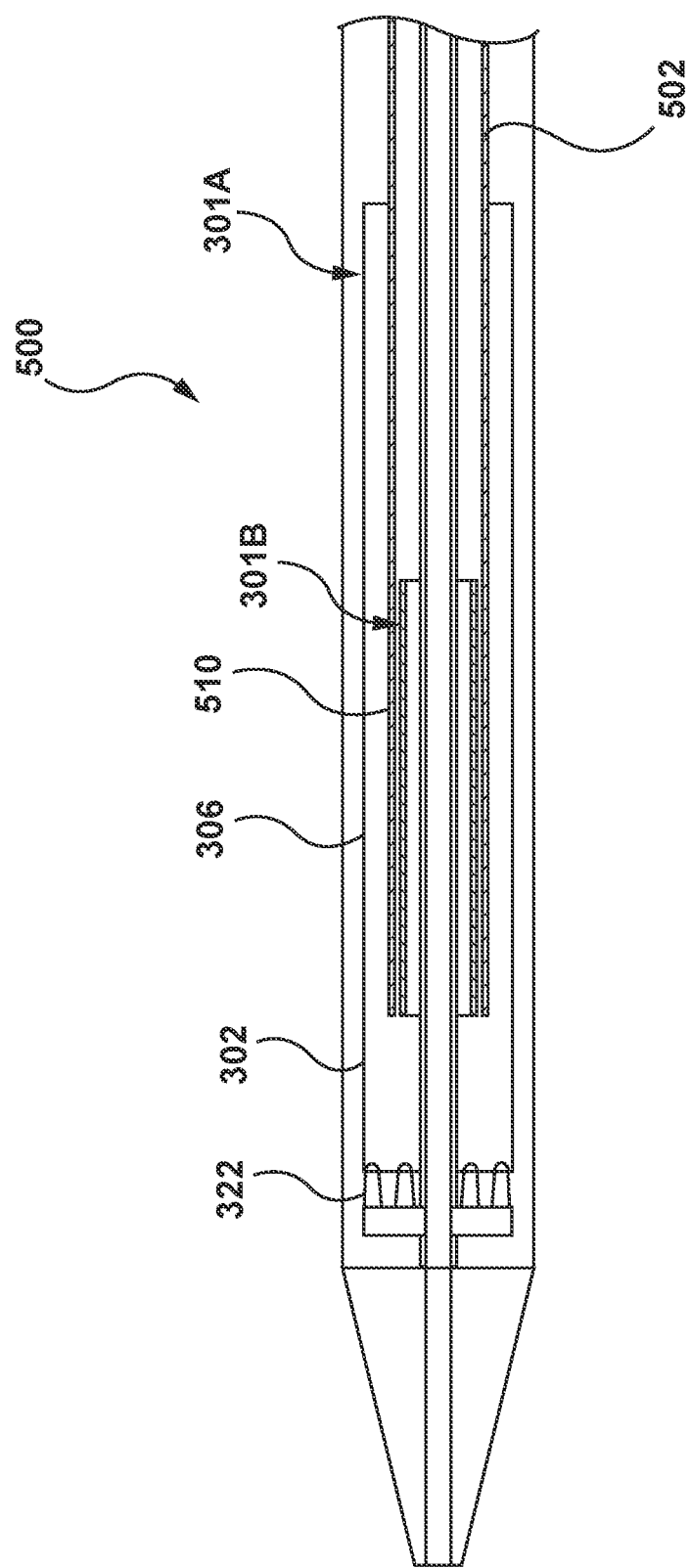
FIG. 23 depicts an illustration of a side view of the stent-graft prosthesis of FIG. 20 in situ, wherein the stent-graft prosthesis is disposed on a distal portion of a delivery system in a radially compressed configuration, according to embodiments hereof.

Referring now to FIG. 23, the stent-graft prosthesis 300 is disposed on a distal portion of the delivery system 500 in the radially compressed configuration. As described above, the delivery system 500 includes at least the outer sheath 502 and the inner shaft 504. The proximal end 311 of the outer stent-graft prosthesis 301A may be releasably coupled to the tip capture mechanism 506. The delivery system 500 of FIGS. 23-25 further includes an intermediate shaft 510 for radially constraining the inner stent-graft 301B in the radially compressed configuration. The outer stent-graft 301A is mounted on the intermediate shaft 510 and the outer sheath 502 encapsulates, covers, or restrains the outer stent-graft 301A in the radially compressed configuration for delivery thereof. The delivery system 500 is advanced to a desired treatment location of an aneurysm AN in a vessel VS. In embodiments hereof, the delivery system 500 may be similar to the Captiva Delivery System, manufactured by Medtronic Vascular, Inc. of Santa Rosa, California, or a delivery system as described in U.S. Patent Application Publication No. 2009/0276027 to Glynn, or U.S. Pat. No. 8,882,828 to Kinkade et al., each of which is incorporated by reference herein in its entirety.

Figure 24A:
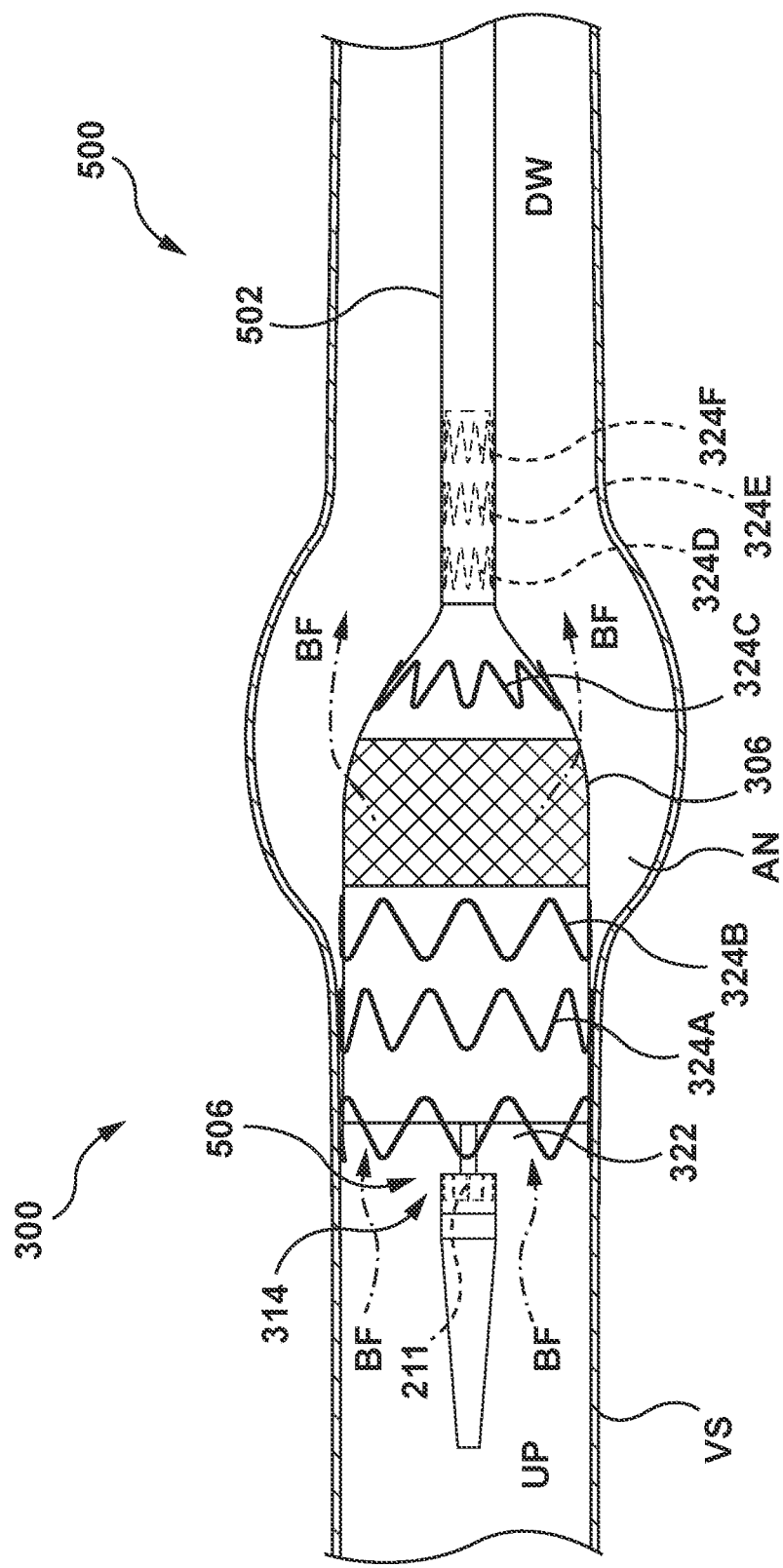
FIG. 24A depicts an illustration of a side view of the stent-graft prosthesis of FIG. 20 in situ, in a partially expanded configuration, according to embodiments hereof.
Figure 24B:
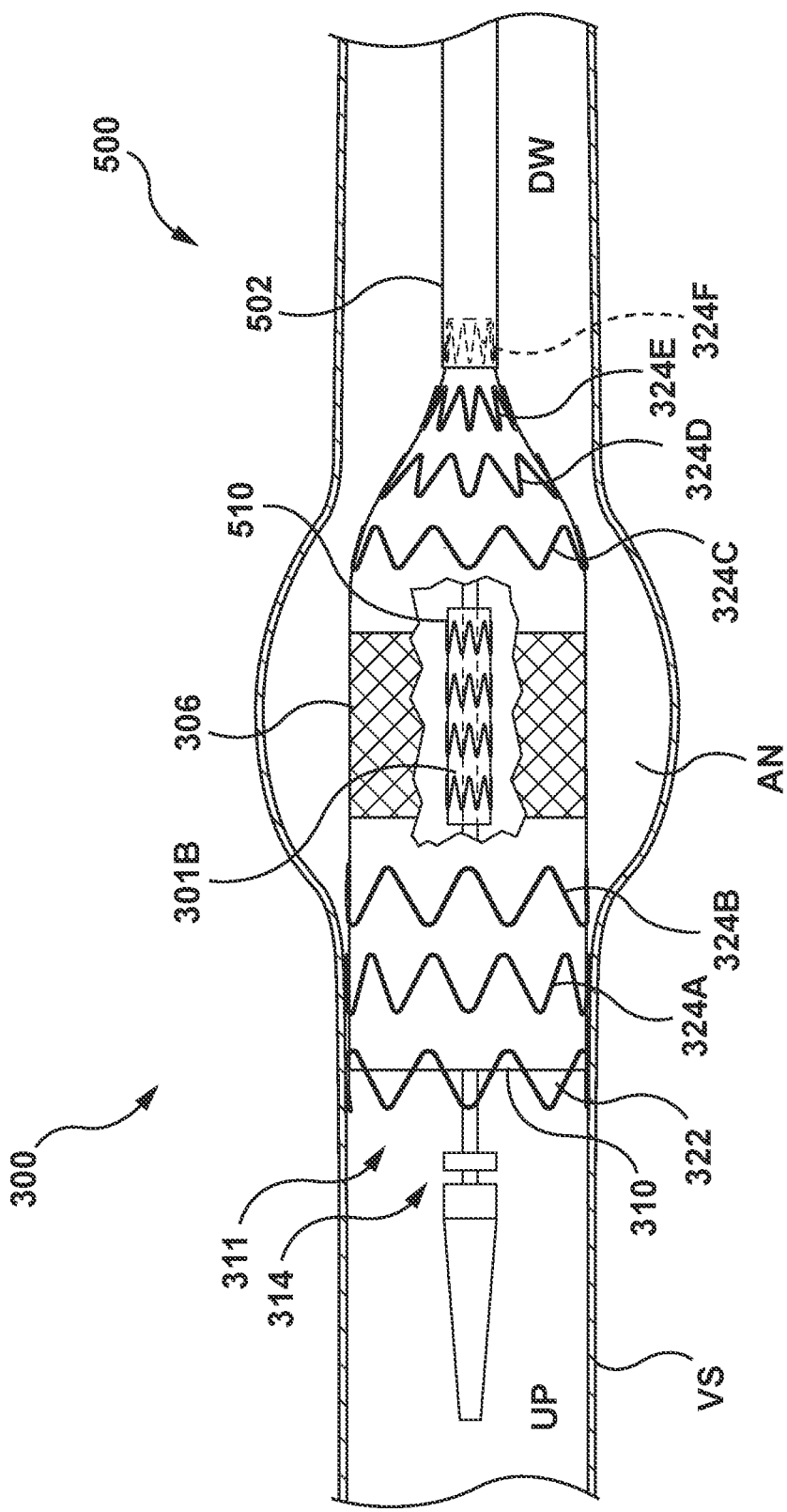
FIG. 24B depicts an illustration of a side view of the stent-graft prosthesis of FIG. 20 in situ, with a portion of the outer stent-graft cut-away, in a partially expanded configuration, according to embodiments hereof.

Once the stent-graft prosthesis 300 is at the desired treatment location within the vessel VS, the outer stent-graft 301A may be deployed from the delivery system 500. The outer sheath 502 of the delivery system 500 is retracted to release a portion the outer stent-graft 301A. The released portion of the outer stent-graft prosthesis 301A radially expands within the vessel VS and the outer stent-graft 301A transitions to a partially expanded configuration, as shown in FIG. 24A. Referring to FIG. 24B, a portion of the outer stent-graft 301A has been cut-away so as to see the inner stent-graft 301B and the intermediate shaft 510 disposed therein.

Still referring to FIGS. 24A-24B, at least the distal end 313 of the outer stent-graft 301A is restrained in the radially compressed state by the outer sheath 502. At the deployment stage shown in FIGS. 24A-24B, the portion of the outer stent-graft 301A restrained by the outer sheath 502 also includes the body stents 324D-224F. As can be seen in FIGS. 24A-24B, a portion of the outer stent-graft 301A, extending from the seal stent 322 to the second body stent 324B is in the radially expanded configuration. Between the radially expanded portion and the portion restrained within the outer sheath 502 is a tapered portion tapering from the radially expanded configuration to the radially compressed configuration restrained within the outer sheath 502.

When in the partially expanded configuration of FIGS. 24A-24B, and prior to thereto, the outer stent-graft 301A at least partially occludes the lumen LU of the vessel VS. Thus, blood flow does not pass within the lumen LU of the vessel VS around the outside of the outer stent-graft 301A. Thus, blood flow enters within the graft lumen 314 of the graft material 302 via an opening at the first end 310 of the graft material 302. However, as explained above, blood entering the graft lumen 314 of the graft material 302 in a conventional stent-graft prosthesis would not be able to escape the graft lumen 314, thereby possibly resulting in "windsocking" or a "windsock" effect. However, with the outer stent-graft 301A, blood that enters the graft lumen 314 of the graft material 302 can exit through the mesh portion/ports 306, as shown by the arrows BF in FIG. 23. Thus, blood from an upstream side UP of the outer stent-graft 301A is permitted to travel into the outer stent-graft 301A, out of the outer stent-graft 301A through the mesh portion/ports 306 to the downstream side DW of the outer stent-graft 301A. More precisely, blood on the upstream side UP of the outer stent-graft 301A enters the graft lumen 314 through the opening at the first end 310 of the graft material 302, travels through the graft lumen 314 of the outer stent-graft 301A, and exits to the downstream side DW of the outer stent-graft 301A through the mesh portion/ports 306. The exit of the blood flow through the mesh portion/ports 306 relieves pressure build-up within the outer stent-graft 301A, which enables more precise positioning of the outer stent-graft 301A. Further, the flow of blood through the mesh portion/ports 306 from the upstream side UP to the downstream side DW of the outer stent-graft 301A provides blood supply to vessels downstream of the outer stent-graft 301A.

Figure 25:
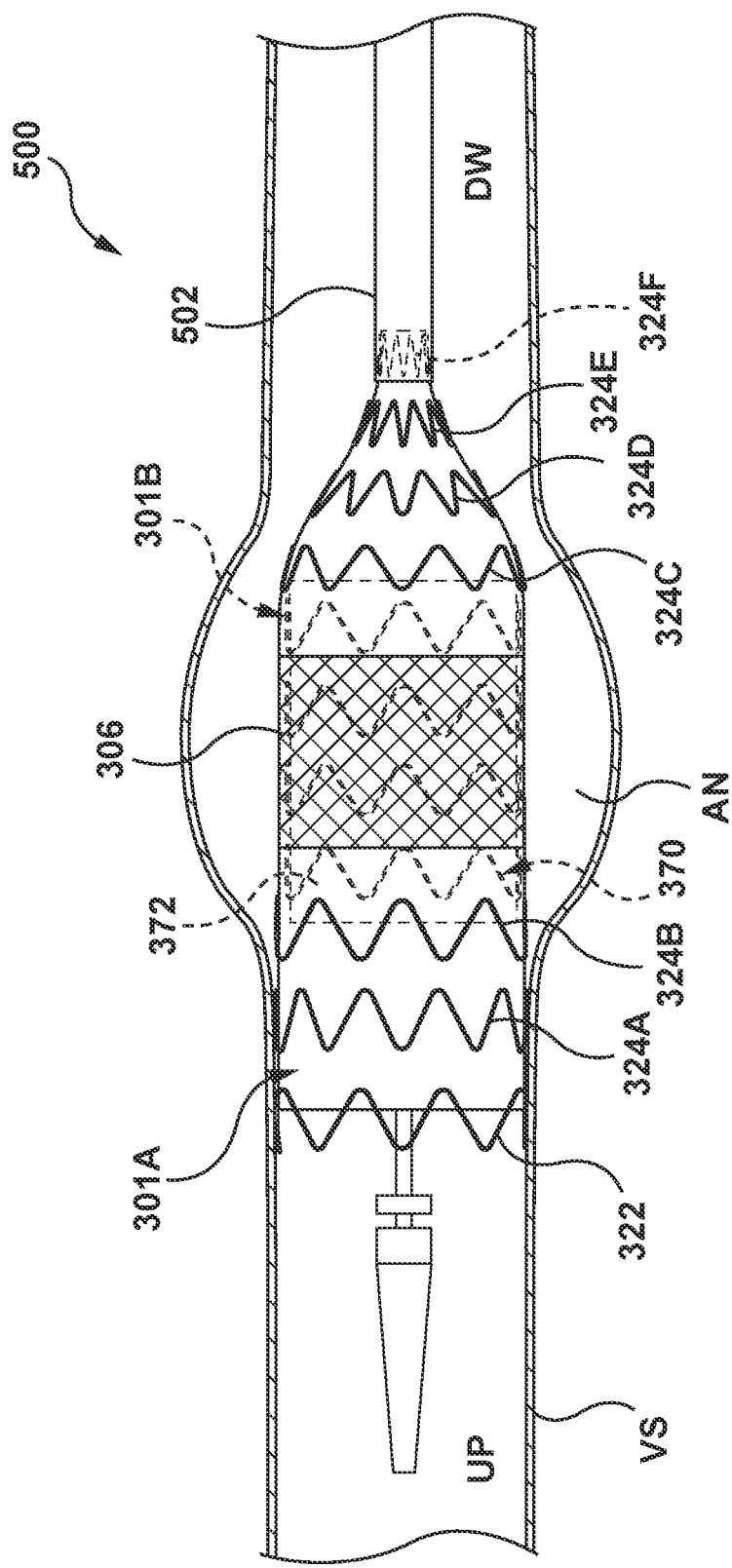
FIG. 25 depicts an illustration of a side view of the stent-graft prosthesis of FIG. 20 in situ, in a partially expanded configuration with the inner stent-graft radially expanded to close the ports thereof, according to embodiments hereof.

Similar to the embodiments described above, as the outer sheath 502 of the delivery system 500 is further retracted from around the outer stent-graft 301A, the outer stent-graft 301A is sufficiently stable to close the mesh portion/port 306. At this stage, the intermediate shaft 510 may be retracted proximally, thereby releasing the inner stent-graft 301B, which radially expands to cover the mesh portion/ports 306, as shown in FIG. 25. Radial expansion of the inner stent-graft 301B covers the mesh portion/ports 306, thereby preventing blood flow from exiting the graft lumen 314 through the graft portion/ports 306.

Figure 26:
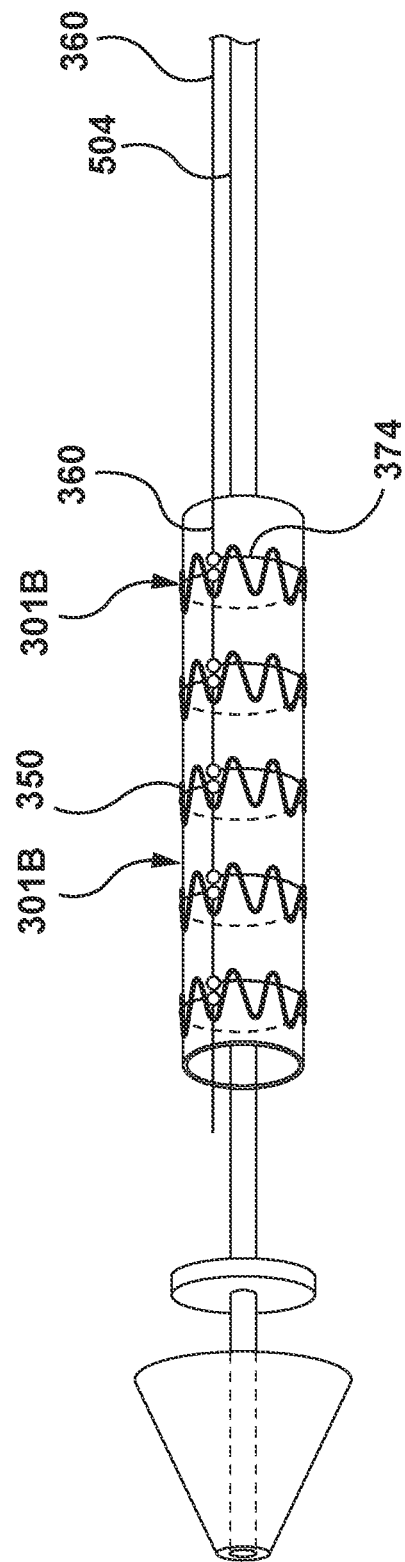
FIG. 26 depicts an illustration of another embodiment of an inner stent-graft of the stent-graft prosthesis of FIG. 20 in a radially compressed configuration with circumferentially constraining sutures, according to embodiments hereof.

In another embodiment, shown in FIG. 26, rather than the inner stent-graft 301B being held in an intermediate shaft 510 of the delivery system 300, the inner stent-graft 301B may be held in the radially compressed configuration by circumferentially constraining sutures 350 and a release or trigger wire 360. As shown in FIG. 26 a plurality of circumferentially restraining sutures 350 may be utilized to radially compress the inner stent-graft 301B. The circumferentially restraining sutures may be any embodiment shown in U.S. Patent Publication No. 2013/0289713, assigned to Medtronic Vascular, Inc., the contents of which are incorporated by reference herein, or other diameter reducing ties or sutures, as known to those skilled in the art. In such an embodiment, when the outer stent-graft 301A is at the stage of deployment such that it is desired for the inner stent-graft 301B to be deployed, the trigger wire is retracted proximally to release the circumferentially restraining sutures, thereby enabling the inner stent-graft to self-expand to cover the mesh portion/ports 306 of the outer stent-graft 301A.

Final deployment of the stent-graft prosthesis 300 is achieved by retracting the outer sheath 502 to release the second end 313 of the outer stent-graft 301A, resulting in the stent-graft prosthesis 300 shown in FIG. 21 or FIG. 22 disposed within the vessel in a radially expanded configuration, with the inner stent-graft 301B covering the mesh portion/ports 306 of the outer stent-graft 301A.

FIGS. 27-30 illustrate a stent-graft prosthesis 400 according to an embodiment hereof. It is noted the stent-graft prosthesis 400 is essentially the same as the stent-graft prosthesis 200 of FIGS. 10-18, except that the stent-graft prosthesis 400 adds a skirt 480 that is not included in the stent-graft prosthesis 200. Therefore, not all of the details of the stent-graft prosthesis 400 will be described, and the description of these details with respect to the stent-graft prosthesis 200, or any of the other embodiments disclose herein, is incorporated into this description of the stent-graft prosthesis 400. Accordingly, the stent-graft prosthesis 400 includes a graft material 402, a frame 404, and openings or ports 406 extending from an inner surface 418 to an outer surface 420 of the graft material 402. The stent-graft prosthesis 400 has a radially compressed configuration for delivery, a radially expanded configuration when deployed, and a partially expanded configuration when transitioning between the radially compressed and the radially expanded configurations. When the stent-graft prosthesis 400 is in the radially expanded configuration at a desired treatment location, the stent-graft prosthesis 400 is configured to bypass a vessel abnormality such as an aneurysm within a body vessel. While described herein as configured to bypass an aneurysm, such as an abdominal aortic aneurysm, this is by way of example and not limitation, and the stent-graft prosthesis 400 may be configured to support/bypass other vessel abnormalities such as, but not limited to dissections and transections.

The graft material 402 is of a generally tubular shape having a central longitudinal axis LA, a first end or edge 410, a second end or edge 412, and a graft lumen or central passage 414 extending from the first end 410 to the second end 412. Similarly, the stent-graft prosthesis 400 includes first, proximal or upstream end or edge 411 a second, distal, or downstream end or edge 413. The frame 404 of the stent-graft prosthesis 400 includes a sealing or seal stent 422 and a plurality of body stents 424 (i.e., body stents 424A-424G in the non-limiting embodiment shown). The seal stent 422 and body stents 424 may also be referred to as frame members. Similar to the embodiment of FIGS. 10-18 the stent-graft prosthesis 400 includes an internal port closing stent 440 to close the ports 406 during deployment. The seal stent 422, each of the body stents 424, and the port closing stent 440 are self-expanding and each includes a radially compressed state, a partially expanded state, and a radially expanded state. Accordingly, the seal stent 422, each of the body stents 424, and the port closing stent 440 are constructed from self-expanding materials as described previously. The seal stent 422 and the body stents 424 are coupled to the graft material 402 by stitches or sutures, or other suitable methods. As explained above, the port closing stent 440 is coupled to the inner surface 418 of the graft material 402, as explained in more detail below.

Figure 27:
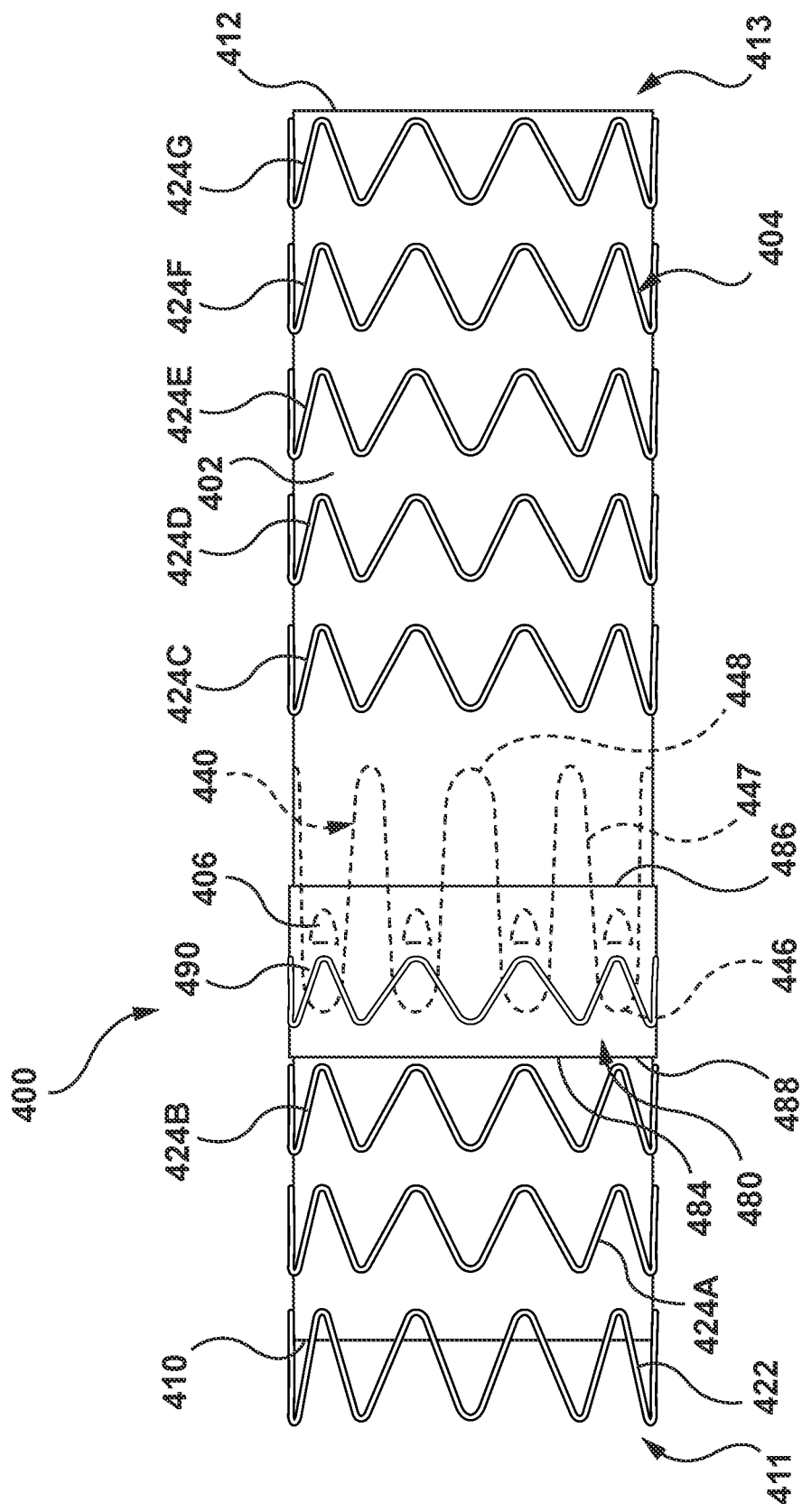
FIG. 27 depicts a schematic side view illustration of a stent-graft prosthesis in a radially expanded configuration according to another embodiment hereof.

As briefly noted above, the stent-graft prosthesis 400 includes a skirt 480. The skirt 480 is attached to the outer surface 420 of the graft material 402. As seen in FIG. 27, the skirt 480 includes graft material 482 having a first end 484 attached to the outer surface 402 of the graft material 402 along a joint 488. The graft material 482 of the skirt 480 further includes a second end 486 distal of the first end 484. The skirt 480 is located on the graft material 402 such that the first end 484 is proximal of the ports 406 and is of sufficient length such that the second end 486 is distal of the ports 406. In some embodiments, the skirt 480 may include a stent 490 attached to the graft material 480 of the skirt 480. However, the stent 490 is optional and is not required.

The port closing stent 440 of the stent-graft prosthesis 400 is similar to the port closing stent 240 of the stent-graft prosthesis 200. However, due to the skirt 480, the port closing stent 440 does not need to have graft material attached to it like the graft material 242 of the port closing stent 240 of the embodiment of FIGS. 10-18. Similar to the port closing stent 240, upstream crowns 446 of the port closing stent 440 are attached to the interior surface 418 of the graft material 402, and the downstream crowns 448 are not attached to the graft material 402. Further, the port closing stent 440 is relatively long, e.g. in the range of about 8 to about 30 mm, or about 10 mm to about 25 mm, or about 15 mm to about 20 mm, such that it is delayed in being released from the outer sheath 502 of the delivery systems, as described above with respect to the port closing stent 240.

Figure 28:
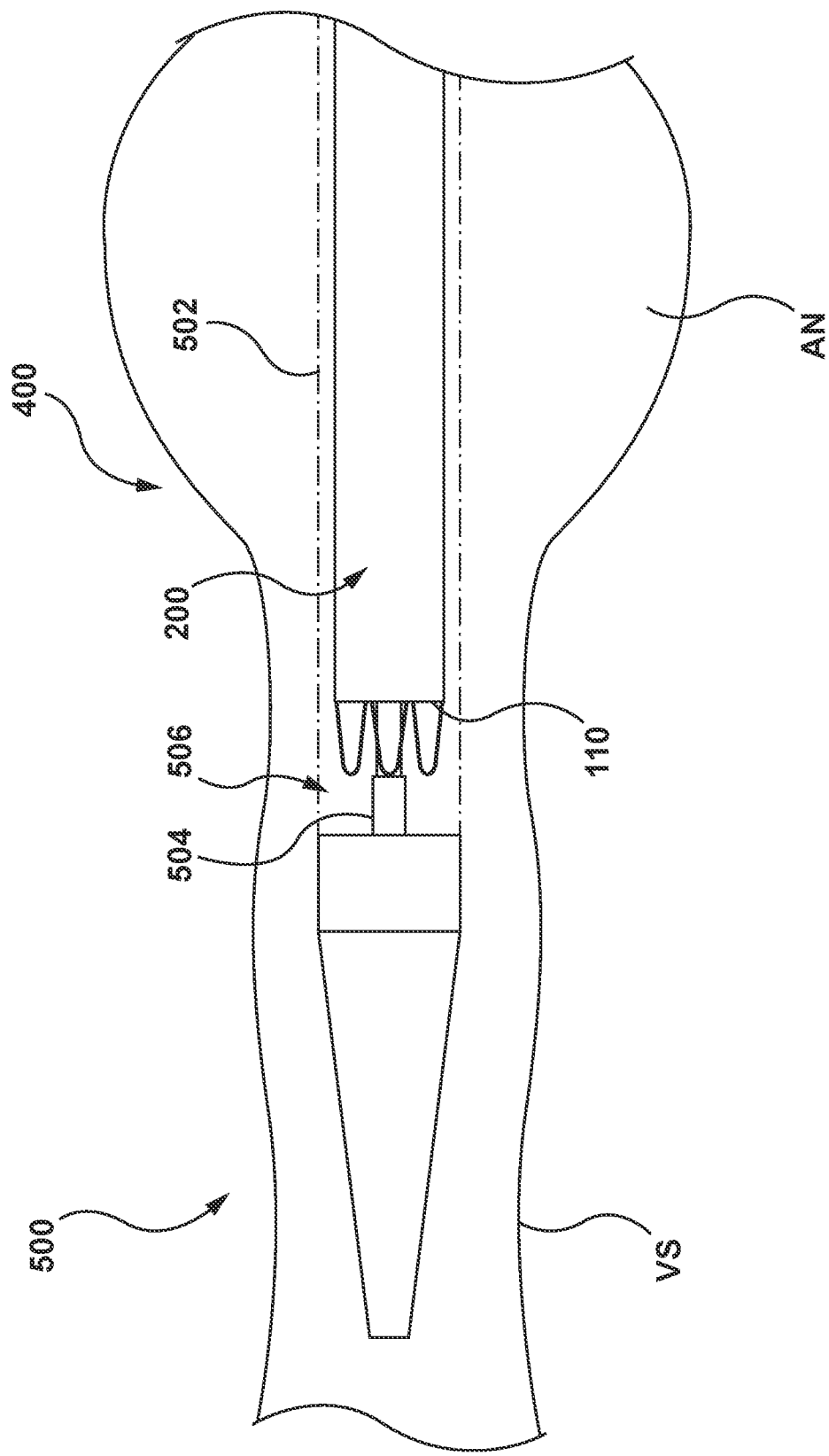
FIG. 28 depicts an illustration of a side view of the stent-graft prosthesis of FIG. 27 in situ, wherein the stent-graft prosthesis is disposed on a distal portion of a delivery system in a radially compressed configuration, according to embodiments hereof.

With the understanding of the stent-graft prosthesis 400, the operation of the stent-graft prosthesis 400 will now be explained with reference to FIGS. 28-30. Referring now to FIG. 28, the stent-graft prosthesis 400 is disposed on a distal portion of the delivery system 500 in the radially compressed configuration. As described above, the delivery system 500 includes at least the outer sheath 502 and the inner shaft 504. The stent-graft prosthesis 400 is mounted on the inner shaft 504 and the outer sheath 502 encapsulates, covers, or restrains the stent-graft prosthesis 400 in the radially compressed configuration for delivery thereof. The delivery system 500 is advanced to a desired treatment location of an aneurysm AN in a vessel VS. In embodiments hereof, the delivery system 500 may be similar to the Captiva Delivery System, manufactured by Medtronic Vascular, Inc. of Santa Rosa, California, or a delivery system as described in U.S. Patent Application Publication No. 2009/0276027 to Glynn, or U.S. Pat. No. 8,882,828 to Kinkade et al., each of which is incorporated by reference herein in its entirety.

Once the stent-graft prosthesis 400 is at the desired treatment location within the vessel VS, the stent-graft prosthesis 400 may be deployed from the delivery system 500. The outer sheath 502 of the delivery system 500 is retracted to release a portion the stent-graft prosthesis 400. The released portion of the stent-graft prosthesis 400 radially expands within the vessel VS and the stent-graft prosthesis 400 transitions to a partially expanded configuration, as shown in FIG. 29. Still referring to FIG. 29, at least the distal end 413 of the stent graft prosthesis 400 is restrained in the radially compressed state by the outer sheath 502.

Figure 29:
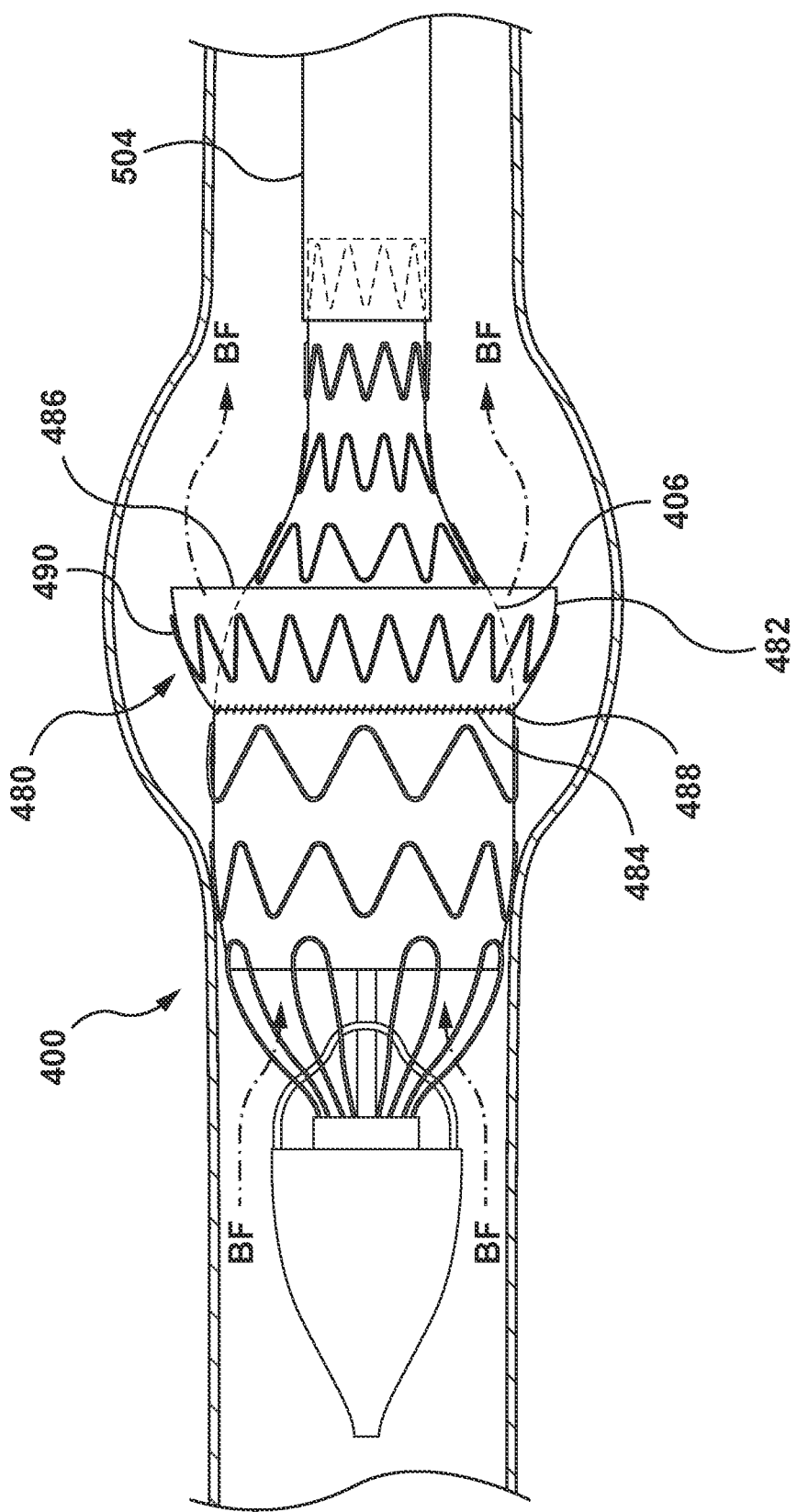
FIG. 29 depicts an illustration of a side view of the stent-graft prosthesis of FIG. 27 in situ, in a partially expanded configuration, according to embodiments hereof.

When in the partially expanded configuration of FIG. 29, and prior to thereto, the stent-graft prosthesis 400 occludes the lumen LU of the vessel VS. Thus, blood flow does not pass within the lumen LU of the vessel VS around the outside of the stent-graft prosthesis 400. Thus, blood flow enters within the graft lumen 414 of the graft material 402 via an opening at the first end 410 of the graft material 402. However, as explained above, blood entering the graft lumen 414 in a conventional stent-graft prosthesis would not be able to escape the graft lumen 414, thereby possibly resulting in "windsocking" or a "windsock" effect. However, with the stent-graft prosthesis 400, blood that enters the graft lumen 414 of the graft material 402 can exit through the ports 406, as shown in FIG. 29. Thus, blood from an upstream side UP of the stent-graft prosthesis 400 is permitted to travel into the stent-graft prosthesis 400, out of the stent-graft prosthesis 400 through the ports 406 to the downstream side DW of the stent-graft prosthesis 400, as shown in FIG. 29 and explained herein and above.

Still referring to FIG. 29, the ports 406 are disposed under the skirt 480. However, because the distal portion of the stent-graft prosthesis 400 is still in the radially compressed configuration, the skirt 480 does not block blood flow BF from exiting through the ports 406, as shown by the arrows BF in FIG. 29. Further, as noted above, in some embodiments, the skirt 480 may include a stent 490 to maintain the skirt 480 radially distanced from the ports 406 when the ports 406 are in a taper portion of the stent-graft prosthesis 400 due to the distal portion of the stent-graft prosthesis being in the radially compressed configuration. Although FIG. 29 shows the skirt flaring radially outward in the distal direction, this flaring is not necessary. In an embodiment without flaring, the skirt 480 is radially expanded to at least the extent of the body stent 424B. However, because the body stents 424C-424G are not fully deployed and the port closing stent 440 is radially constrained, the ports 406 are open, thereby allowing blood flow out of the ports 406.

Still referring to FIG. 29, at this stage of deployment, the proximal or upstream crowns 446 of the port closing stent 440 are attached to the inner surface 418 of the graft material 402 upstream of the ports 406, but the downstream crowns 448 of the port closing stent 440 remain radially constrained within the outer sheath 502 of the delivery system 500. Thus, the portion of the port closing stent 440 adjacent the ports 406 is not radially expanded against the inner surface 418 of the graft material 402. Thus, blood can flow around the port closing stent 440 and exit the graft lumen 414 through the ports 406. As noted above, the port closing stent 440 does not need to include graft material, but it can.

Figure 30:
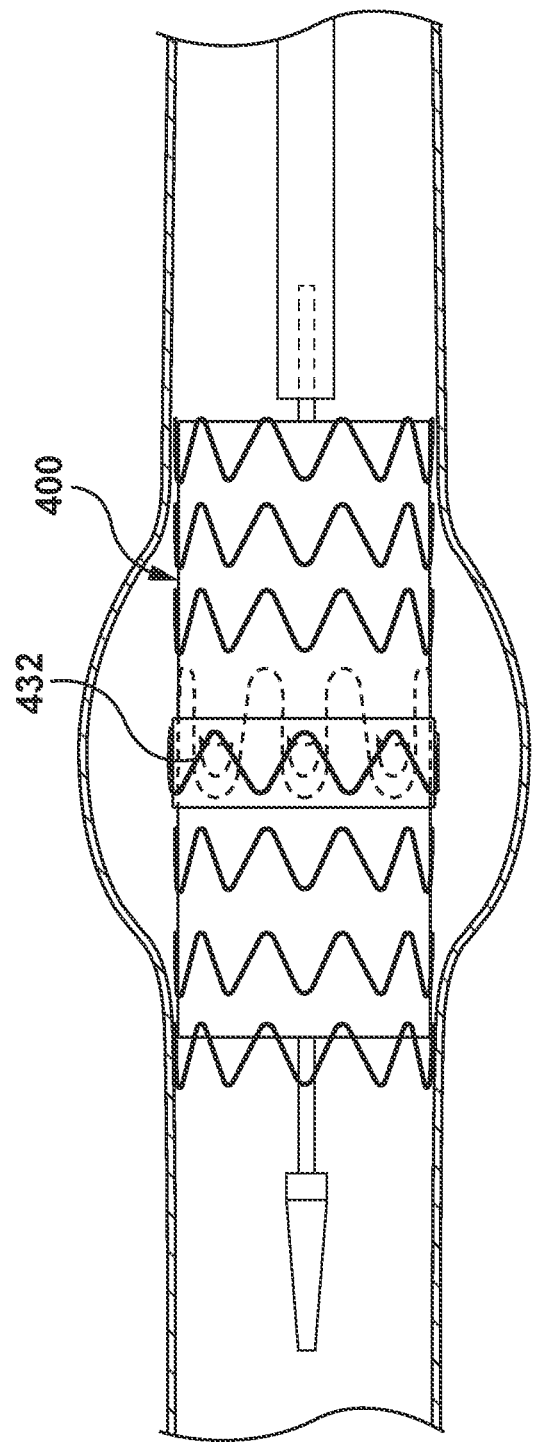
FIG. 30 depicts an illustration of a side view of the stent-graft prosthesis of FIG. 27 in situ, in a radially expanded, deployed configuration with the port closing stent thereof closing the ports thereof, according to embodiments hereof.

As the outer sheath 502 of the delivery system 500 is further retracted from around the stent-graft prosthesis 400, the downstream crowns 448 of the port closing stent 440 are eventually released from the outer sheath 502, thereby enabling self-expansion of the port closing stent 440, as shown in FIG. 30. With the port closing stent 440 radially expanded, it presses against the inner surface 418 of the graft material 402, which pushes the graft material 402 against the graft material 482 of the skirt 480, thereby blocking the ports 406. Final deployment of the stent-graft prosthesis 400 is achieved by retracting the outer sheath 502 to release the second end 413 of the stent-graft prosthesis 400. With the stent-graft prosthesis 400 fully deployed, blood flow enters the opening at the first end 411 of the stent-graft prosthesis 400, flows through the graft lumen 214, is prevented from exiting through the ports 406, and exits the graft lumen 414 through the opening at the second end 413 of the stent-graft prosthesis 400. The delivery system 500 may then be removed from the patient, leaving the stent-graft prosthesis 400 implanted such that blood flow bypasses the aneurysm AN.

Although the stent graft prosthesis 400 of FIGS. 27-30 has been described with a port closing stent that is similar to the one described with respect to FIGS. 10-18, those skilled in the art would recognize that the port closing stents described above with respect to FIGS. 19A-19C and FIG. 20 may be utilized instead, with or without the port closing stent graft material described with respect to those embodiments. Thus, the port closing stents described above with respect to those embodiments are hereby incorporated into the description of the stent-graft prosthesis 400. Similarly, instead of a port closing stent as described in FIGS. 10-18, 19A-19C, and 20, the inner stent-graft described with respect to FIGS. 21-26 may be used. In other words, any of the embodiments described above can be modified to include the skirt described with respect to FIGS. 27-30.

Figure 31:
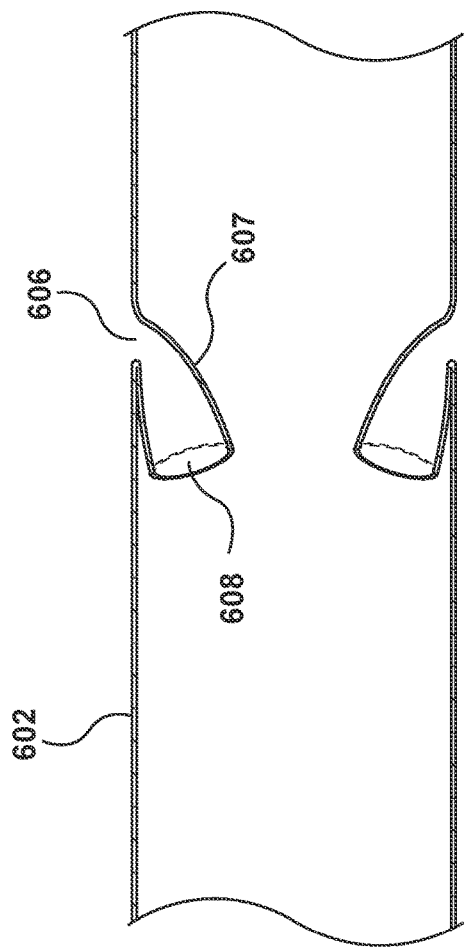
FIG. 31 depicts a schematic illustration of a port including an internal valve accordingly to embodiments hereof.
Figure 32:
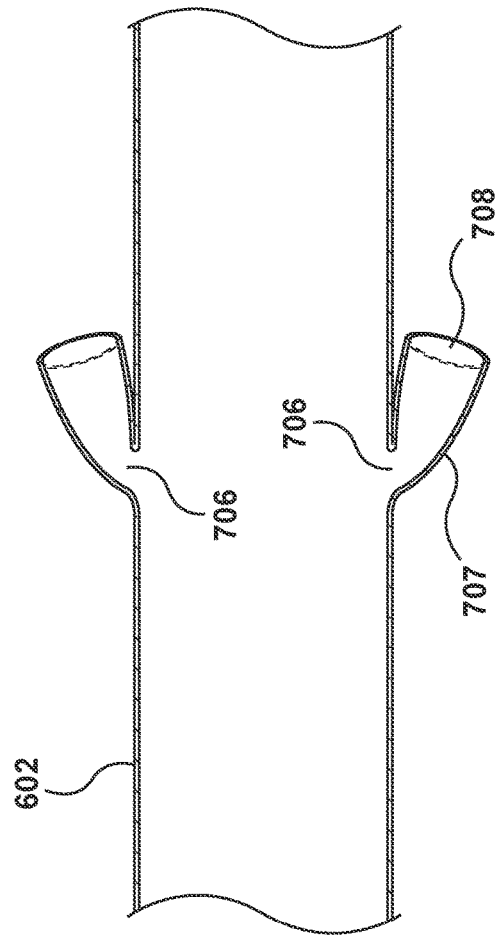
FIG. 32 depicts a schematic illustration of a port including an internal valve accordingly to embodiments hereof.

FIGS. 31 and 32 schematically show alternative embodiments of ports including pockets or valves that can be used with any of the embodiments described above.

FIG. 31 shows a portion of a stent-graft prosthesis including graft material 602 and ports 606. Two (2) ports 606 are shown in FIG. 31, but it is understood that FIG. 31 is a schematic cross-sectional view, and more ports 606 may be provided around the circumference of the stent-graft prosthesis. The ports 606 of FIG. including a graft material 607 extending inwardly from the ports 606 in a conical or distally tapered shape, with an opening 608 at a proximal end and the port 606 are the distal end. Thus, blood can flow in the proximal opening 608 and out of the port 606.

FIG. 32 shows a portion of a stent-graft prosthesis including graft material 702 and ports 706. Two (2) ports 706 are shown in FIG. 32, but it is understood that FIG. 32 is a schematic cross-sectional view, and more ports 706 may be provided around the circumference of the stent-graft prosthesis. The ports 706 of FIG. 32 include a graft material 707 extending outwardly and distally from the ports 706 in a conical or flared shape, with an opening 708 at a distal end and the port 706 are the distal end. Thus, blood can flow in the port 706 and out of the distal opening 708. Although the graft material 707 is shown expanded, those skilled in the art would recognize that the graft material 707 is loose such that it can be expanded via blood flow therethrough. Thus, in the embodiment of FIG. 32, a port closing stent or inner stent-graft may not be need to close the port 706. Instead, when the stent-graft prosthesis is radially expanded, the body stent pressed the graft material 702 of the stent-graft prosthesis against the graft material 707 of the valve, thereby preventing blood flow through the graft material 707.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above described exemplary embodiments, but should be defined only in accordance with the appended claims and their equivalents. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. A stent-graft prosthesis comprising:
a graft material having a tubular construction, the graft material including a proximal end, a distal end, and a graft lumen extending between the proximal end and the distal end;
a frame coupled to the graft material;
a port disposed between the proximal end and the distal end of the graft material, wherein the port enables blood flow from within the graft lumen to exit the graft lumen; and
a port closing stent disposed within the graft lumen, wherein the port closing stent includes a first longitudinal edge attached to an inner surface of the graft material and a second longitudinal edge opposite the first longitudinal edge, where the second longitudinal edge defines a circumference, and wherein none of the circumference of the second longitudinal edge is attached to the graft material,
wherein the port closing stent includes a first configuration wherein the second longitudinal edge of the port closing stent is spaced radially inward of the graft material and the port so as to permit blood flow from the graft lumen through the port and a second configuration wherein the second longitudinal edge of the port closing stent blocks flow from the graft lumen through the port.

2. The stent-graft prosthesis of claim 1, wherein the port closing stent includes port closing graft material attached thereto such that in the second configuration the port closing graft material blocks the port.

3. The stent-graft prosthesis of claim 1, wherein in the first configuration, the second longitudinal edge of the port closing stent is in a radially compressed configuration, and in the second configuration, the second longitudinal edge of the port closing stent is in a radially expanded configuration.

4. The stent-graft prosthesis of claim 3, wherein the second longitudinal edge of the port closing stent is configured to be maintained in the radially compressed configuration by a sheath of a delivery system such that retraction of the sheath causes the second longitudinal edge of the port closing stent to radially expand to the radially expanded configuration.

5. The stent-graft prosthesis of claim 3, wherein the second longitudinal edge of the port closing stent is maintained in the radially compressed configuration by a circumferentially restraining suture and a trigger wire such that moving the trigger wire causes the second longitudinal end of the port closing stent to radially expand to the radially expanded configuration.

6. The stent-graft prosthesis of claim 1, wherein the first longitudinal edge of the port closing stent is a proximal edge of the port closing stent and the second longitudinal edge of the port closing stent is a distal edge of the port closing stent.

7. The stent-graft prosthesis of claim 1, wherein the first longitudinal edge of the port closing stent is a distal edge of the port closing stent and the second longitudinal edge of the port closing stent is a proximal edge of the port closing stent.

8. The stent-graft prosthesis of claim 1, further comprising a skirt coupled to an outer surface of the graft material, wherein the skirt covers the port.

9. The stent graft-prosthesis of claim 1, wherein the port closing stent comprises a ring having a plurality of proximal crowns, a plurality of distal crowns, and a plurality of struts connecting the plurality of proximal crowns to the distal plurality of distal crowns.

10. The stent-graft prosthesis of claim 9, wherein the distal crowns of the port closing stent are attached to the graft material and the proximal crowns of the port closing stent are not attached to the graft material.

11. The stent-graft prosthesis of claim 10, wherein a majority length of the plurality of struts between the proximal crowns and the distal crowns are not attached to the graft material.

* * * * *